United States Patent
Tohnishi et al.

(10) Patent No.: US 7,256,192 B2
(45) Date of Patent: Aug. 14, 2007

(54) AROMATIC DIAMIDE DERIVATIVES, CHEMICALS FOR AGRICULTURAL OR HORTICULTURAL USE AND USAGE THEREOF

(75) Inventors: Masanori Tohnishi, Sakai (JP); Eiji Kohno, Bisai (JP); Hayami Nakao, Kawachinagano (JP); Tateki Nishida, Tondabayashi (JP); Takashi Furuya, Izumisano (JP); Toshiaki Shimizu, Kawachinagano (JP); Akira Seo, Hashimoto (JP); Kazuyuki Sakata, Kawachinagano (JP); Shinsuke Fujioka, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 978 days.

(21) Appl. No.: 10/168,334

(22) PCT Filed: Dec. 22, 2000

(86) PCT No.: PCT/JP00/09146

§ 371 (c)(1),
(2), (4) Date: Sep. 20, 2002

(87) PCT Pub. No.: WO01/46124

PCT Pub. Date: Jun. 28, 2001

(65) Prior Publication Data

US 2004/0009982 A1 Jan. 15, 2004

(30) Foreign Application Priority Data

Dec. 22, 1999 (JP) .............................. 11-365408

(51) Int. Cl.
*A01N 43/58* (2006.01)
*A61K 31/50* (2006.01)

(52) U.S. Cl. ............ 514/247; 514/252.03; 514/255.05; 514/275; 514/354; 514/616; 514/617; 544/224; 544/238; 544/333; 544/405; 546/314; 546/304; 564/154; 564/155; 564/156

(58) Field of Classification Search ................. 556/419; 514/247, 354, 617, 252.03, 255.05, 275, 514/616; 544/238, 224, 333; 546/314; 564/155
See application file for complete search history.

(56) References Cited

U.S. PATENT DOCUMENTS 6,864,289 B1 * 3/2005 Tohnishi et al. ............ 514/617

FOREIGN PATENT DOCUMENTS

| EP | 799825 | * 10/1997 |
|---|---|---|
| EP | 0919542 | 6/1999 |
| EP | 919542 | * 6/1999 |
| HU | P0201555 | 8/2002 |
| WO | WO 99/44992 | 9/1999 |
| WO | WO 9944992 | * 9/1999 |
| WO | WO 01/00575 | 1/2001 |

* cited by examiner

Primary Examiner—Thurman K. Page
Assistant Examiner—Chukwuma Nwaonicha
(74) Attorney, Agent, or Firm—Paul E. White; Manelli Denison & Selter PLLC

(57) ABSTRACT

The present invention relates to an aromatic diamide derivative represented by the general formula (I):

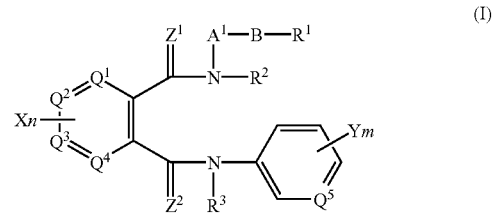

(I)

[$A^1$ is optionally substituted ($C_1$-$C_8$)alkylene group, ($C_3$-$C_8$)alkenylene group or the like, B is —O— or —N($R^4$)— (wherein $R^4$ is H, ($C_1$-$C_6$)alkyl, halo($C_1$-$C_6$)alkyl or the like), $R^1$ is H, ($C_1$-$C_6$)alkyl, optionally substituted phenyl, optionally substituted heterocyclic group, or the like, $R^2$ and $R^3$ are each H, ($C_3$-$C_6$) cycloalkyl or —$A^2$—$R^8$ ($A^2$ is —C(=O)—, —C(=S)— or —C(=$NR^9$)—, $R^8$ and $R^9$ are each H, ($C_1$-$C_6$)alkyl or the like), $Q^1$ to $Q^5$ are each carbon or nitrogen, X and Y are each halogen, cyano, nitro, ($C_3$-$C_6$)cycloalkyl, optionally substituted phenyl, optionally substituted heterocyclic group, or the like, n is 0 to 4, m is 1 to 5, and $Z^1$ and $Z^2$ are each O or S] or a salt thereof, an agricultural and horticultural chemical, and a usage of the chemical. The agricultural and horticultural chemicals of the present invention exhibit remarkable controlling effects against various insect pests such as agricultural, forest and horticultural insect pests, and stored grain insect pests, etc., which injure paddy rice, fruit trees, vegetables, other crop plants, flowers and ornamental plants, and the like.

7 Claims, No Drawings

AROMATIC DIAMIDE DERIVATIVES, CHEMICALS FOR AGRICULTURAL OR HORTICULTURAL USE AND USAGE THEREOF

TECHNICAL FIELD

The present invention relates to aromatic diamide derivatives or salts thereof; an agricultural and horticultural chemical, in particular, an agricultural and horticultural insecticide, which contains said compound as an active ingredient; and a usage of the chemical.

BACKGROUND ART

JP-A-11-240857 discloses a compound analogous to the aromatic diamide derivative of the present invention but does not describes working examples, physical properties and the like with respect to the compound of the present invention.

DISCLOSURE OF THE INVENTION

The production of agricultural and horticultural crops and the like is still badly damaged by insect pests and the like, and the development of a novel agricultural and horticultural chemical, in particular, agricultural and horticultural insecticide is desired because of, for example, the appearance of insect pests resistant to existing chemicals. In addition, because of the increased population of aged farmers, and the like, various labor-saving application methods are desired and the development of an agricultural and horticultural chemical having properties suitable for the application methods is desired.

The present inventors earnestly investigated in order to develop a novel agricultural and horticultural chemical, and consequently found that the aromatic diamide derivative represented by the general formula (I) of the present invention is a novel compound not known in any literature, and the present inventors found a novel use of said derivative as an agricultural and horticultural chemical, in particular, an agricultural and horticultural insecticide and their effective usage, whereby the present invention has been accomplished.

That is, the present invention relates to an aromatic diamide derivative represented by the general formula (I):

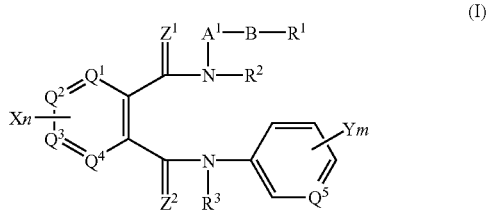
(I)

{wherein $A^1$ is a $(C_1$-$C_8)$alkylene group; a substituted $(C_1$-$C_8)$alkylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group; a $(C_3$-$C_8)$alkenylene group; a substituted $(C_3$-$C_8)$alkenylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group; a $(C_3$-$C_8)$alkynylene group; or a substituted $(C_3$-$C_8)$alkynylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group, any of the saturated carbon atoms in the above-mentioned $(C_1$-$C_8)$alkylene group, substituted $(C_1$-$C_8)$alkylene group, $(C_3$-$C_8)$alkenylene group, substituted $(C_3$-$C_8)$alkenylene group, $(C_3$-$C_8)$alkynylene group or substituted $(C_3$-$C_8)$alkynylene group being able to have a $(C_2$-$C_5)$alkylene group bonded thereto as a substituent, to form a $(C_3$-$C_6)$cycloalkane ring, and any two of the carbon atoms in the above-mentioned $(C_1$-$C_8)$alkylene group, substituted $(C_1$-$C_8)$alkylene group, $(C_3$-$C_8)$alkenylene group and substituted $(C_3$-$C_8)$alkenylene group being able to form a $(C_3$-$C_6)$cycloalkane ring or a $(C_3$-$C_6)$cycloalkene ring together with an alkylene group or an alkenylene group, B is —C— or —N($R^4$)— (wherein $R^4$ is a hydrogen atom; a $(C_1$-$C_6)$alkyl group; a halo$(C_1$-$C_6)$alkyl group; a $(C_3$-$C_6)$alkenyl group; a halo$(C_3$-$C_6)$alkenyl group; a $(C_3$-$C_6)$alkynyl group; a $(C_3$-$C_6)$cycloalkyl group; a $(C_1$-$C_6)$alkylcarbonyl group; a halo$(C_1$-$C_6)$alkylcarbonyl group; a $(C_1$-$C_6)$alkoxycarbonyl group; a phenylcarbonyl group; a substituted phenylcarbonyl group having on the ring one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, and di$(C_1$-$C_6)$alkylamino groups whose $(C_1$-$C_6)$alkyl groups may be the same or different; a phenyl$(C_1$-$C_4)$alkoxycarbonyl group; a substituted phenyl$(C_1$-$C_4)$alkoxycarbonyl group having on the ring one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, and di$(C_1$-$C_6)$alkylamino groups whose $(C_1$-$C_6)$alkyl groups may be the same or different; a phenyl$(C_1$-$C_4)$alkyl group; or a substituted phenyl$(C_1$-$C_4)$alkyl group having on the ring one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-

$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups), $R^1$ is a hydrogen atom; a ($C_1$-$C_6$)alkyl group; a halo($C_1$-$C_6$)alkyl group; a ($C_1$-$C_4$)alkoxy($C_1$-$C_4$)alkyl group; a ($C_1$-$C_4$)alkylthio($C_1$-$C_4$)alkyl group; a ($C_2$-$C_6$)alkenyl group; a halo($C_2$-$C_6$)alkenyl group; a ($C_3$-$C_6$)alkynyl group; a halo($C_3$-$C_6$)alkynyl group; a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; —P(=$W^1$)(—$OR^5$)(—$OR^6$) (wherein $W^1$ is an oxygen atom or a sulfur atom, and each of $R^1$ and $R^6$, which may be the same or different, is a hydrogen atom; a ($C_1$-$C_6$)alkyl group; a halo($C_1$-$C_6$)alkyl group; a ($C_1$-$C_4$)alkoxy($C_1$-$C_4$)alkyl group; a ($C_1$-$C_4$)alkylthio($C_1$-$C_4$)alkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono ($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring); —C(=$W^1$)—N($R^5$)($R^6$) (wherein $W^1$, $R^1$ and $R^6$ are as defined above, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring, and $R^5$ being able to bind to $R^4$ to form a 5- to 8-membered ring that may contain two or three atoms which may be the same or different and are selected from oxygen atom, sulfur atom and nitrogen atom, between adjacent carbon atoms constituting the ring); —C(=$W^1$)—$R^5$ (wherein $W^1$ and $R^5$ areas defined above); —C(=$W^1$)—$W^1$—$R^7$ (wherein $W^1$s, which may be the same or different, are as defined above, and $R^7$ is a ($C_1$-$C_6$)alkyl group; a halo($C_1$-$C_6$)alkyl group; a ($C_1$-$C_4$)alkoxy($C_1$-$C_4$)alkyl group; a ($C_1$-$C_4$)alkylthio($C_1$-$C_4$)alkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups); —$SO_2$—$R^7$ (wherein $R^7$ is as defined above); —$SO_2$—N($R^5$)($R^6$) (wherein $R^5$ and $R^6$ are as defined above, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring, and $R^5$ being able to bind to $R^4$ to form a 5- to 8-membered ring that may contain three or four atoms which may be the same or different and are selected from oxygen atom, sulfur atom and nitrogen atom, between adjacent carbon atoms constituting the ring); —N($R^5$) ($R^6$) (wherein $R^5$ and $R^6$ are as defined above, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring, and $R^5$ being able to bind to $R^4$ to form a 5- to 8-membered ring that may contain two or three atoms which may be the same or different and are selected from oxygen atom, sulfur atom and nitrogen atom, between adjacent carbon atoms constituting the ring); or —N=C($R^5$)$R^6$ (wherein $R^1$ and $R^6$ are as defined above, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring); in the case of B being —N($R^4$)—, $R^1$ being able to be —O$R^5$ (wherein $R^5$ is as defined above), —C($W^2$)—N($R^5$)$R^6$ (wherein $W^2$ is =CH—$NO_2$, =N—$NO_2$ or =N—CN, and $R^5$ and $R^6$ are as defined above, $R^5$ or $R^6$ being able to bind to $R^4$ to form a 5- to 8-membered ring that may contain two or three atoms which may be the same or different and are selected from oxygen atom, sulfur atom and nitrogen atom, between adjacent carbon atoms constituting the ring) or —C($W^2$)—$W^1$—$R^7$ (wherein $W^1$, $W^2$ and $R^7$ are as defined above, $R^7$ being able to bind to $R^4$ to form a 5- to 8-membered ring that may contain two or three atoms which may be the same or different and are selected from oxygen atom, sulfur atom and nitrogen atom, between adjacent carbon atoms constituting the ring), and $R^1$ being able to bind to $A^1$ to form a 5- to 8-membered ring that may contain one or two atoms which may be the same or different and are selected from oxygen atom, sulfur atom and nitrogen atom, between adjacent carbon atoms constituting the ring, each of $R^2$ and $R^3$, which may be the same or different, is a hydrogen atom, a ($C_3$-$C_6$)cycloalkyl group or —$A^2$—$R^8$ (wherein $A^2$ is —C(=O)—, —C(=S)—, —C(=N$R^9$)— (wherein $R^9$ is a hydrogen atom, a ($C_1$-$C_6$)alkyl group, a ($C_1$-$C_6$)alkoxy group, a mono($C_1$-$C_6$)alkylamino group, a di($C_1$-$C_6$)alkylamino group whose ($C_1$-$C_6$)alkyl groups may be the same or different, a ($C_1$-$C_6$)alkoxycarbonyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups), a ($C_1$-$C_8$)alkylene group, a halo ($C_1$-$C_8$)alkylene group, a ($C_3$-$C_6$)alkenylene group, a halo ($C_3$-$C_6$)alkenylene group, a ($C_3$-$C_6$)alkynylene group or a halo($C_3$-$C_6$)alkynylene group, (1) in the case of $A^2$ being —C(=O)—, —C(=S)— or —C(=N$R^9$)— (wherein $R^9$ is as defined above), $R^8$ is a hydrogen atom; a ($C_1$-$C_6$)alkyl group; a halo($C_1$-$C_6$)alkyl group; a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups; or —$A^3$—$R^{10}$ (wherein $A^3$ is —O—, —S— or —N($R^{11}$)— (wherein $R^{11}$ is a hydrogen atom; a ($C_1$-$C_6$)alkylcarbonyl group; a halo($C_1$-$C_6$)alkylcarbonyl group; a ($C_1$-$C_6$)alkoxycarbonyl group; a phenylcarbonyl group; a substituted phenylcarbonyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups; a phenyl($C_1$-$C_4$)alkoxycarbonyl group; or a substituted phenyl($C_1$-$C_4$)alkoxycarbonyl group having on the ring one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups), and $R^{10}$ is a ($C_1$-$C_6$)alkyl group; a halo($C_1$-$C_6$)alkyl group; a ($C_3$-$C_6$)alkenyl group; a halo($C_3$-$C_6$)alkenyl group; a ($C_3$-$C_6$)alkynyl group; a halo($C_3$-$C_6$)alkynyl group; a ($C_3$-$C_6$) cycloalkyl group; a halo($C_3$-$C_6$)cycloalkyl group; a ($C_1$-$C_6$) alkylcarbonyl group; a halo($C_1$-$C_6$)alkylcarbonyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono ($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups), (2) in the case of $A^2$ being a $(C_1-C_8)$alkylene group, a halo$(C_1-C_8)$alkylene group, a $(C_3-C_6)$alkenylene group, a halo$(C_3-C_6)$alkenylene group, a $(C_3-C_6)$alkynylene group or a halo$(C_3-C_6)$alkynylene group, $R^8$ is a hydrogen atom; a halogen atom; a cyano group; a nitro group; a $(C_3-C_6)$cycloalkyl group; a halo$(C_3-C_6)$cycloalkyl group; a $(C_1-C_6)$alkoxycarbonyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; or —$A^4$—$R^{12}$ (wherein $A^4$ is —O—, —S—, —SO—, —SO$_2$—, —N($R^{11}$)— (wherein $R^{11}$ is as defined above), —C(=O)—, or —C(=N—O$R^{13}$) (wherein $R^{13}$ is a hydrogen atom, a $(C_1-C_6)$alkyl group, a halo$(C_1-C_6)$alkyl group, a $(C_3-C_6)$alkenyl group, a halo$(C_3-C_6)$alkenyl group, a $(C_3-C_6)$alkynyl group, a halo$(C_3-C_6)$alkynyl group, a $(C_3-C_6)$cycloalkyl group, a phenyl$(C_1-C_4)$alkyl group, or a substituted phenyl$(C_1-C_4)$alkyl group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups), (i) in the case of $A^4$ being —O—, —S—, —SO—, —SO$_2$— or —N($R^{11}$)— (wherein $R^{11}$ is as defined above), $R^{12}$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_3-C_6)$cycloalkyl group; a halo$(C_3-C_6)$cycloalkyl group; a $(C_1-C_6)$alkylcarbonyl group; a halo$(C_1-C_6)$alkylcarbonyl group; a $(C_1-C_6)$alkoxycarbonyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenyl$(C_1-C_4)$alkyl group; a substituted phenyl$(C_1-C_4)$alkyl group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, (ii) in the case of $A^4$ being —C(=O)— or —C(=NO$R^{13}$) (wherein $R^{13}$ is as defined above), $R^{12}$ is a hydrogen atom; a $(C_1-C_6)$alkyl group; a halo$(C_1-C_6)$alkyl group; a $(C_2-C_6)$alkenyl group; a halo$(C_2-C_6)$alkenyl group; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a mono$(C_1-C_6)$alkylamino group; a di$(C_1-C_6)$alkylamino group whose $(C_1-C_6)$alkyl groups may be the same or different; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenylamino group; a substituted phenylamino group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di($C_1$-$C_6$)alkylamino groups whose ($C_1$-$C_6$)alkyl groups may be the same or different, and ($C_1$-$C_6$)alkoxycarbonyl groups; a phenyloxy group; a substituted phenyloxy group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylthio group; a substituted phenylthio group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups)), further, $R^2$ being able to bind to $A^1$ or $R^1$ to form a 5- to 8-membered ring that may contain one to three atoms which may be the same or different and are selected from oxygen atom, sulfur atom and nitrogen atom, between adjacent carbon atoms constituting the ring, each of $Q^1$ through $Q^5$ is a carbon atom or a nitrogen atom, each of Xs, which may be the same or different, is a halogen atom; a cyano group; a nitro group; a ($C_3$-$C_6$)cycloalkyl group; a halo($C_3$-$C_6$)cycloalkyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^5$—$R^{14}$ (wherein $A^5$ is —O—, —S—, —SO—, —$SO_2$—, —C(=O)—, —C(=$NOR^{13}$) (wherein $R^{13}$ is as defined above), a ($C_1$-$C_6$)alkylene group, a halo($C_1$-$C_6$)alkylene group, a ($C_2$-$C_6$)alkenylene group, a halo($C_2$-$C_6$)alkenylene group, a ($C_2$-$C_6$)alkynylene group or a halo($C_3$-$C_6$)alkynylene group, (1) in the case of $A^5$ being —O—, —S—, —SO— or —$SO_2$—, $R^{14}$ is a halo($C_3$-$C_6$)cycloalkyl group; a halo($C_3$-$C_6$)cycloalkenyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^6$—$R^{15}$ (wherein $A^6$ is a ($C_1$-$C_6$)alkylene group, a halo($C_1$-$C_6$)alkylene group, a ($C_3$-$C_6$)alkenylene group, a halo($C_3$-$C_6$)alkenylene group, a ($C_3$-$C_6$)alkynylene group or a halo($C_3$-$C_6$)alkynylene group, and $R^{15}$ is a hydrogen atom; a halogen atom; a ($C_3$-$C_6$)cycloalkyl group; a halo($C_3$-$C_6$)cycloalkyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo ($C_1$-$C_6$)alkylthio groups, ($C_1$-$C_6$)alkylsulfinyl groups, halo ($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^7$—$R^{16}$ (wherein $A^7$ is —O—, —S—, —SO— or —$SO_2$—, and $R^{16}$ is a ($C_1$-$C_6$)alkyl group; a halo($C_1$-$C_6$)alkyl group; a ($C_3$-$C_6$)alkenyl group; a halo($C_3$-$C_6$)alkenyl group; a ($C_3$-$C_6$)alkynyl group; a halo($C_3$-$C_6$)alkynyl group; a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups), (2) in the case of $A^5$ being —C(=O)— or —C(=NOR$^{13}$)— (wherein $R^{13}$ is as defined above), $R^{14}$ is a ($C_1$-$C_6$)alkyl group; a halo($C_1$-$C_6$)alkyl group; a ($C_2$-$C_6$)alkenyl group; a halo($C_2$-$C_6$)alkenyl group; a ($C_3$-$C_6$)cycloalkyl group; a halo($C_3$-$C_6$)cycloalkyl group; a ($C_1$-$C_6$)alkoxy group; a ($C_1$-$C_6$)alkylthio group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylamino group; a substituted phenylamino group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo ($C_1$-$C_6$)alkylthio groups, ($C_1$-$C_6$)alkylsulfinyl groups, halo ($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, (3) in the case of $A^5$ being a ($C_1$-$C_6$)alkylene group, a halo($C_1$-$C_6$)alkylene group, a ($C_2$-$C_6$)alkenylene group, a halo($C_2$-$C_6$)alkenylene group, a ($C_2$-$C_6$)alkynylene group or a halo($C_3$-$C_6$)alkynylene group, $R^{14}$ is a hydrogen atom; a halogen atom; a ($C_3$-$C_6$)cycloalkyl group; a halo($C_3$-$C_6$)cycloalkyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo ($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, ($C_1$-$C_6$)alkylsulfonyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^8$—$R^{17}$ (wherein $A^8$ is —O—, —S—, —SO— or —SO$_2$—, and $R^{17}$ is a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or -$A^{9'}$-R (wherein $A^9$ is a ($C_1$-$C_6$)alkylene group, a halo($C_1$-$C_6$)alkylene group, a ($C_2$-$C_6$)alkenylene group, a halo($C_9$-$C_6$)alkenylene group, a ($C_2$-$C_6$)alkynylene group or a halo($C_3$-$C_6$)alkynylene group, and $R^{18}$ is a hydrogen atom; a halogen atom; a ($C_3$-$C_6$)cycloalkyl group; a halo($C_3$-$C_6$)cycloalkyl group; a ($C_1$-$C_6$)alkoxy group; a halo($C_1$-$C_6$)alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyloxy group; a substituted phenyloxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylthio group; a substituted phenylthio group having one or more substituents which may be the same or different and are selected from halogen atoms, cyano group, nitro group, ($C_1$-$C_6$)alkyl groups, halo ($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-

$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups)), n is an integer of 0 to 4, further, two adjacent Xs on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, each of Ys, which may be the same or different, is a halogen atom; a cyano group; a nitro group; a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo ($C_1$-$C_6$)alkyl groups, ($C_1$-$C_6$)alkoxy groups, halo($C_1$-$C_6$) alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^5$—$R^{14}$ (wherein $A^5$ and $R^{14}$ are as defined above), further, two adjacent Ys on the aromatic ring being able to be taken together to represent a fused ring that may have one or more substituents which may be the same or different and are selected from halogen atoms; ($C_1$-$C_6$)alkyl groups; halo($C_1$-$C_6$)alkyl groups; ($C_1$-$C_6$)alkoxy groups; halo($C_1$-$C_6$)alkoxy groups; ($C_1$-$C_6$)alkylthio groups; halo($C_1$-$C_6$)alkylthio groups; ($C_1$-$C_6$)alkylsulfinyl groups; halo($C_1$-$C_6$)alkylsulfinyl groups; ($C_1$-$C_6$)alkylsulfonyl groups; halo($C_1$-$C_6$)alkylsulfonyl groups; phenyl group; substituted phenyl groups having one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups; heterocyclic groups; and substituted heterocyclic groups having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, m is an integer of 1 to 5, and each of $Z^1$ and $Z^2$ is an oxygen atom or a sulfur atom} or a salt thereof, an agricultural and horticultural chemical containing aromatic diamide derivative as an active ingredient, and a usage of the same.

MODE FOR CARRYING OUT THE INVENTION

In the definition of the general formula (I) shown for the aromatic diamide derivative or salt thereof of the present invention, the term "halogen atom" means a chlorine atom, a bromine atom, an iodine atom or a fluorine atom. The term "($C_1$-$C_6$)alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The term "halo($C_1$-$C_6$)alkyl" means a substituted and linear or branched alkyl group of 1 to 6 carbon atoms having as the substituent (s) one or more halogen atoms which may be the same or different. The term "($C_1$-$C_8$)alkylene" means a linear or branched alkylene group of 1 to 8 carbon atoms, such as methylene, ethylene, propylene, trimethylene, dimethylmethylene, tetramethylene, isobutylene, dimethylethylene, octamethylene or the like. As "the 5- to 8-membered ring which $R^1$ and $R^6$ (or $R^2$ and $A^1$ or $R^1$)form by their binding to each other, i.e., the 5- to 8-membered ring that may contain one or two (or one to three) atoms which may be the same or different and are selected from oxygen atom, sulfur atom and nitrogen atom, between adjacent carbon atoms constituting the ring" or "the 5- to 8-membered ring which $R^5$ (or $R^6$ or $R^7$) and $R^4$ form by their binding to each other, i.e., the 5- to 8-membered ring that may contain two or three, or three or four atoms which may be the same or different and are selected from oxygen atom, sulfur atom and nitrogen atom, between adjacent carbon atoms constituting the ring", there can be exemplified azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring, dithiazine ring, etc.

The "heterocyclic group" includes, for example, pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group and pyrazolyl group. The "fused ring" includes, for example, naphthalene, tetrahydronaphthalene, indene, indane, quinoline, quinazoline, indole, indoline, chroman, isochroman, benzodioxane, benzodioxole, benzofuran, dihydrobenzofuran, benzothiophene, dihydrobenzothiophene, benzoxazole, benzothiazole, benzimidazole and indazole.

The salt of the aromatic diamide derivative of the general formula (I) of the present invention includes, for example, inorganic acid salts such as hydrochloride, sulfate, nitrate, phosphate and the like; organic acid salts such as acetate, fumarate, maleate, oxalate, methanesulfonate, benzenesulfonate, p-toluenesulfonate and the like; salts with a sodium ion, potassium ion, calcium ion or the like.

The aromatic diamide derivative of the general formula (I) or salt thereof of the present invention contains one or more asymmetric carbon atoms or asymmetric centers in its structural formula in some cases and has two or more optical isomers and diastereomers in some cases. The present invention also includes all of the individual optical isomers and mixtures consisting of these isomers in any ratio. The aromatic diamide derivative of the general formula (I) or salt thereof of the present invention has two geometrical isomers due to a carbon-carbon double bond or a carbon-nitrogen double bond in its structural formula in some cases. The present invention also includes all of the individual geometrical isomers and mixtures consisting of these isomers in any ratio. The present invention also includes hydrates of said compound, depending on the kind of the compound.

Preferable examples of the aromatic diamide derivative of the general formula (I) or salt thereof of the present invention are aromatic diamide derivatives in which $A^1$ is a $(C_1-C_4)$alkylene group, B is —O— or —N($R^4$)— (wherein $R^4$ is a hydrogen atom or a $(C_1-C_3)$alkyl group), $R^1$ is a hydrogen atom, a $(C_1-C_3)$alkyl group, a phenyl$(C_1-C_3)$alkyl group, a substituted phenyl$(C_1-C_3)$alkyl group, a $(C_1-C_3)$alkylcarbonyl group, a halo$(C_1-C_3)$alkylcarbonyl group, a $(C_1-C_3)$alkoxycarbonyl group, a mono$(C_1-C_3)$alkylaminocarbonyl group, a di$(C_1-C_3)$alkylaminocarbonyl group whose $(C_1-C_3)$alkyl groups may be the same or different, a $(C_1-C_3)$alkylsulfonyl group, a mono$(C_1-C_3)$alkylaminosulfonyl group, a di$(C_1-C_3)$alkylaminosulfonyl group whose $(C_1-C_3)$alkyl groups may be the same or different, a di$(C_1-C_3)$alkoxyphosphono group whose $(C_1-C_3)$alkyl groups may be the same or different, or a di$(C_1-C_3)$alkoxythiophosphono group whose $(C_1-C_3)$alkyl groups may be the same or different, each of $R^2$ and $R^3$ is a hydrogen atom or a $(C_1-C_3)$alkyl group, each of $Q^1$ through $Q^4$ is a carbon atom, X is a halogen atom, a nitro group, a halo$(C_1-C_6)$alkyl group, a halo$(C_1-C_6)$alkoxy group or a halo$(C_1-C_6)$alkylthio group, n is an integer of 0 to 2, $Q^5$ is a carbon atom or a nitrogen atom, each of Ys, which may be the same or different, is a halogen atom, a $(C_1-C_3)$alkyl group, a halo$(C_1-C_3)$alkyl group, a $(C_1-C_3)$alkoxy group, a halo$(C_1-C_3)$alkoxy group, a halo$(C_1-C_3)$alkylthio group or a halo$(C_1-C_3)$alkoxyhalo$(C_1-C_3)$alkoxy group, m is an integer of 1 to 3, each of $Z^1$ and $Z^2$ is an oxygen atom; or salts thereof.

The aromatic diamide derivative of the general formula (I) or salt thereof of the present invention can be produced, for example, by the production process illustrated below. In the present invention, the production can be carried out also by, for example, the process disclosed in JP-A-11-240857. A process for the production, however, is not limited to these production processes.

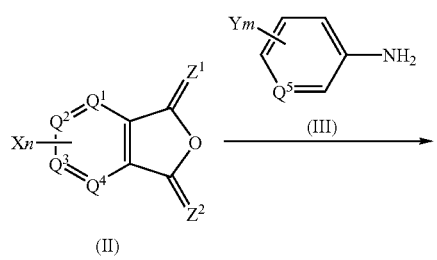

Production process 1.

(II)

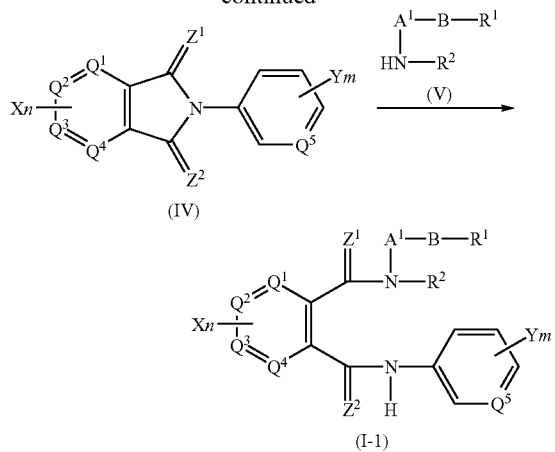

wherein $R^1$, $R^2$, $R^3$, $A^1$, B, $Q^1$ through $Q^5$, X, n, Y, m, $Z^1$ and $Z^2$ are as defined above.

An aromatic diamide derivative of the general formula (I-1) can be obtained by allowing an aromatic carboxylic acid anhydride derivative of the general formula (II) to react with an aromatic amine of the general formula (III) in the presence of an inert solvent to obtain an aromatic imide derivative of the general formula (IV), and allowing said aromatic imide derivative (IV) to react with an amine of the general formula (V) after or without isolation of the aromatic imide derivative (IV).

(1). General formula (II)→general formula (IV)

As the inert solvent usable in this reaction, any inert solvent may be used so long as it does not markedly inhibit the progress of the reaction. There can be exemplified inert solvents including aromatic hydrocarbons such as benzene, toluene, xylene, etc.; halogenated hydrocarbons such as methylene chloride, chloroform, carbon tetrachloride, etc.; chlorinated aromatic hydrocarbons such as chlorobenzene, dichlorobenzene, etc.; acyclic or cyclic ethers such as diethyl ether, dioxane, tetrahydrofuran, etc.; esters such as ethyl acetate, etc.; amides such as dimethylformamide, dimethylacetamide, etc.; acids such as acetic acid, etc.; dimethyl sulfoxide; 1,3-dimethyl-2-imdazolidinone; and the like. These inert solvents may be used singly or as a mixture thereof.

Since the reaction is an equimolar reaction, it is sufficient that the reactants are used in equimolar amounts, though either of them may be used in excess. If necessary, the reaction may be carried out under dehydrating conditions.

As to the reaction temperature, the reaction can be carried out at room temperature to the reflux temperature of the inert solvent used. Although the reaction time is varied depending on the scale of reaction, the reaction temperature, etc., it may be properly chosen in the range of several minutes to 48 hours.

After completion of the reaction, the desired compound is isolated from the reaction system containing the desired compound by a conventional method, and if necessary, purified by recrystallization, column chromatography, etc., whereby the desired compound can be produced. The desired compound can be subjected to the subsequent reaction step without isolation from the reaction system.

The aromatic carboxylic acid anhydride derivative of the general formula (II) can be produced by any of the processes described in J. Org. Chem., 52, 129 (1987), J. Am. Chem. Soc., 51, 1865 (1 to 29), ditto 63, 1542 (1941), etc. The aromatic amine of the general formula (III) can be produced by any of the processes described in J. Org. Chem., 29, 1 (1964), Angew. Chem. Int. Ed. Engl., 24, 871 (1985), Synthesis, 1984, 667, Journal of Chemical Society of Japan, 1973, 2351, German Patent Laid-Open DE-2606982, JP-A-1-90163, etc.

(2). General formula (IV)→general formula (I-1)

As an inert solvent usable in this reaction, those exemplified as the inert solvent usable in (1) can be exemplified.

Since the reaction is an equimolar reaction, it is sufficient that the reactants are used in equimolar amounts, though the amine of the general formula (V) may be used in excess.

As to the reaction temperature, the reaction can be carried out at room temperature to the reflux temperature of the inert solvent used. Although the reaction time is varied depending on the scale of reaction, the reaction temperature, etc., it may be properly chosen in the range of several minutes to 48 hours.

After completion of the reaction, the desired compound is isolated from the reaction system containing the desired compound by a conventional method, and if necessary, purified by recrystallization, column chromatography, etc., whereby the desired compound can be produced.

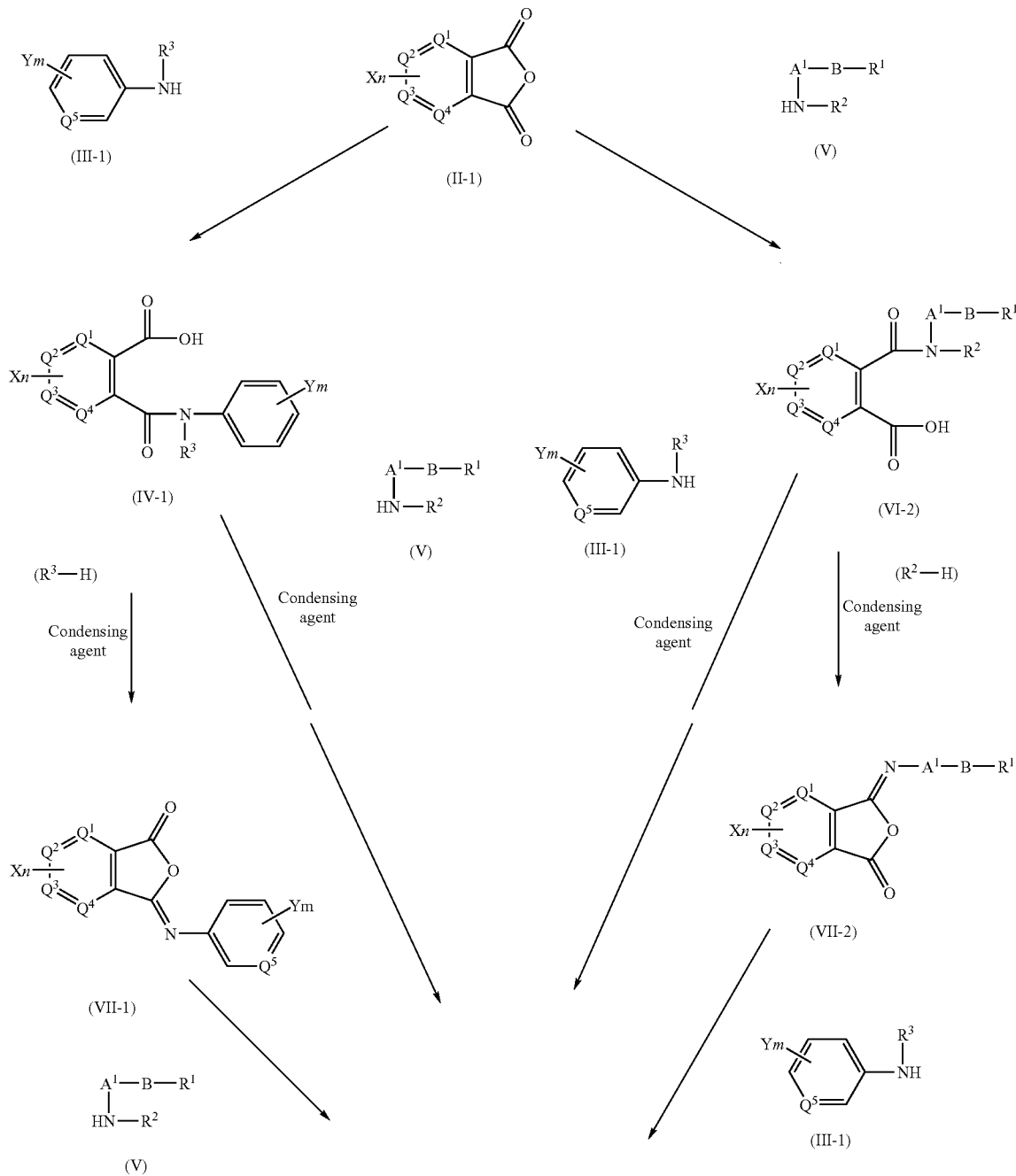

-continued

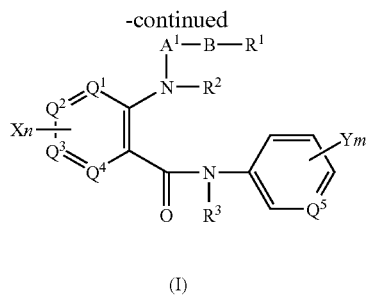

(I)

wherein $R^1$, $R^2$, $R^3$, $A^1$, B, $Q^1$ through Q, X, n, Y, m, $Z^1$ and $Z^2$ are as defined above.

An aromatic diamide derivative of the general formula (I) can be produced by allowing an aromatic carboxylic acid anhydride derivative of the general formula (II-1) to react with an amine of the general formula (V) in the presence of an inert solvent to obtain a phthalamide of the general formula (VI-2), and treating this aromatic amide (VI-2) as follows after or without isolation. When $R^2$ of the aromatic amide (VI-2) is a hydrogen atom, the aromatic amide (VI-2) is subjected to condensation reaction in the presence of a condensing agent to obtain a compound of the general formula (VII-2), which is allowed to react with an aromatic amine of the general formula (III-1) in the presence of an inert solvent after or without isolation of the compound (VII-2). When $R^2$ of the aromatic amide (VI-2) is other than a hydrogen atom, the aromatic amide (VI-2) is condensed with an aromatic amine of the general formula (III-1) in the presence of a condensing agent.

Alternatively, an aromatic diamide derivative of the general formula (I) can be produced by allowing an aromatic carboxylic acid anhydride derivative of the general formula (II-1) to react with an aromatic amine of the general formula (III-1) in the presence of an inert solvent to obtain an aromatic amide of the general formula (VI-1), and treating the aromatic amide (VI-1) as follows after or without isolation. When $R^3$ of the aromatic amide (VI-1) is a hydrogen atom, the aromatic amide (VI-1) is subjected to condensation reaction in the presence of a condensing agent to obtain a compound of the general formula (VII-1), which is allowed to react with an amine of the general formula (V) in the presence of an inert solvent after or without isolation of the compound (VII-1). When $R^3$ of the aromatic amide (VI-1) is other than a hydrogen atom, the aromatic amide (VI-1) is condensed with an amine of the general formula (V) in the presence of a condensing agent.

(1). General formula (II-1)→general formula (VI-1), or general formula (II-1)→general formula (VI-2)

In the case of either of these reactions, the desired compound can be produced in a manner similar to that described in production process 1-(2).

(2). General formula (VII-1) or general formula (VII-2)→general formula (I)

In the case of this reaction, the desired compound can be produced in a manner similar to that described in production process 1-(2).

(3). General formula (VI-1)→general formula (VII-1), or general formula (VI-2)→general formula (VII-2)

In the case of either of these reactions, the desired compound can be produced according to the process described in J. Med. Chem., 10, 982 (1967).

(4). General formula (VI-1) or general formula (VI-2)→general formula (I)

The desired compound can be produced by allowing an aromatic amide derivative of the general formula (VI-1) or the general formula (VI-2) to react with an amine of the general formula (V) or the general formula (III-1), respectively, in the presence of a condensing agent and an inert solvent. If necessary, the reaction can be carried out in the presence of a base.

The inert solvent used in the reaction includes, for example, tetrahydrofuran, diethyl ether, dioxane, methylene chloride and chloroform.

As the condensing agent used in the reaction, any condensing agent used in conventional amide production may be used. There can be exemplified Mukaiyama reagent (2-chloro-N-methylpyridinium iodide), DCC (1,3-dicyclohexylcarbodiimide), CDI (carbonyldiimidazole) and DEPC (diethyl cyanophosphate). As to the amount of the condensing agent used, the condensing agent may be used in an amount properly chosen in the range of 1 mole to excess moles per mole of the aromatic amide derivative of the general formula (VI-1) or the general formula (VI-2).

The base usable in the reaction includes, for example, organic bases such as triethylamine, pyridine, etc., and inorganic bases such as potassium carbonate, etc. As to the amount of the base used, the base may be used in an amount properly chosen in the range of 1 mole to excess moles per mole of the aromatic amide derivative of the general formula (VI-1) or the general formula (VI-2).

As to the reaction temperature, the reaction can be carried out at 0° C. to the boiling point of the inert solvent used. Although the reaction time is varied depending on the scale of reaction, the reaction temperature, etc., it ranges from several minutes to 48 hours.

After completion of the reaction, the desired compound is isolated from the reaction system containing the desired compound by a conventional method, and if necessary, purified by recrystallization, column chromatography, etc., whereby the desired compound can be produced.

Typical compounds as the aromatic diamide derivative of the general formula (I) or a salt thereof are listed in Table 1 or Table 2 but they are not intended in any way to limit the scope of the present invention. In the following tables, Me indicates methyl, Et ethyl, Pro propyl, Bu butyl, Ph phenyl, Pyr pyridyl, and c- an alicyclic hydrocarbon.

TABLE 1

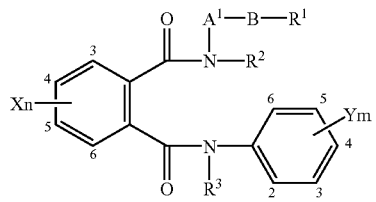

($Z^1 = Z^2 = O$, $R^3 = H$, $Q^1 \sim Q^5 = C$, unless otherwise specified.)

| No. | —$A^1$—B—$R^1$ | $R^2$ | Xn | Ym | Physical property: Melting point ° C. |
|---|---|---|---|---|---|
| 1 | (CH$_2$)NHCO$_2$Pr-i | H | 3-I | 2-Me-4-CF(CF$_3$)$_2$ | 105 |
| 2 | (CH$_2$)NHCO$_2$Pr-i | H | 3-I | 2-Me-4-OCF$_3$ | 200 |
| 3 | (CH$_2$)NHCO$_2$Et | H | 3-I | H | 175 |
| 4 | (CH$_2$)NHCO$_2$Et | H | 3-I | 4-CF$_2$CF$_3$ | 180 |
| 5 | (CH$_2$)NHCO$_2$Me | H | 3-I | H | 200 |
| 6 | (CH$_2$)NHCO$_2$Me | H | 3-I | 2-Me-4-CF$_2$CF$_3$ | 130 |
| 7 | (CH$_2$)NHCO$_2$Me | H | 3-I | 2-Me-4-CF(CF$_3$)$_2$ | 160 |
| 8 | C(Me)$_2$CH$_2$NHCO$_2$Et | H | 3-I | 2-Me-4-CF(CF$_3$)$_2$ | 240 |
| 9 | C(Me)$_2$CH$_2$NHCO$_2$Et | H | 6-I | 2-Me-4-CF(CF$_3$)$_2$ | 140 |
| 10 | C(Me)$_2$CH$_2$NHCO$_2$Et | H | 3-I | 2-Me-4-OCF$_3$ | 155 |
| 11 | C(Me)$_2$CH$_2$NHCO$_2$Et | H | 6-I | 2-Me-4-OCF$_3$ | 220 |
| 12 | C(Me)$_2$CH$_2$NHCO$_2$Me | H | 3-I | 2-Me-4-CF(CF$_3$)$_2$ | 100 |
| 13 | C(Me)$_2$CH$_2$NHCO$_2$Me | H | 6-I | 2-Me-4-CF(CF$_3$)$_2$ | 230 |
| 14 | C(Me)$_2$CH$_2$NHCO$_2$Pr | H | 3-I | 2-Me-4-CF(CF$_3$)$_2$ | 100 |
| 15 | C(Me)$_2$CH$_2$NHCO$_2$Me | H | 3-I | 2-Me-4-OCF$_3$ | 95 |
| 16 | C(Me)$_2$CH$_2$NHCO$_2$Me | H | 6-I | 2-Me-4-OCF$_3$ | 120 |
| 17 | C(Me)$_2$CH$_2$NHCO$_2$Et | H | 3-I | 2-Me | 95 |
| 18 | C(Me)$_2$CH$_2$NHCO$_2$Et | H | 6-I | 2-Me | 120 |
| 19 | C(Me)$_2$CH$_2$NHCO$_2$Et | H | 3-I | 2-Me-4-CF$_2$CF$_3$ | 200 |
| 20 | (CH$_2$)$_3$NHCO$_2$Bu-t | H | 3-I | 2-Me-4-CF(CF$_3$)$_2$ | 145 |
| 21 | (CH$_2$)$_3$NHCO$_2$Me | H | 3-I | 2-Me-4-CF(CF$_3$)$_2$ | 80 |
| 22 | CH(Me)CH$_2$NHCO$_2$Me | H | 3-I | 2-Me-4-CF(CF$_3$)$_2$ | 175 |
| 23 | Q | H | 3-I | 2-Me-4-CF(CF$_3$)$_2$ | 235 |
| 24 | Q | H | 6-I | 2-Me-4-CF(CF$_3$)$_2$ | 225 |
| 25 | Q | H | 3-I | 2-Me-4-OCF$_3$ | 220 |
| 26 | Q | H | 6-I | H | 225 |
| 27 | C(Me)$_2$CH$_2$NHCOPh | H | 3-I | 2-Me-4-CF(CF$_3$)$_2$ | 240 |
| 28 | C(Me)$_2$CH$_2$NHCOMe | H | 3-I | 2-Me-4-CF(CF$_3$)$_2$ | 125 |
| 29 | C(Me)$_2$CH$_2$NHCOPr-c | H | 3-I | 2-Me-4-CF(CF$_3$)$_2$ | 230 |
| 30 | C(Me)$_2$CH$_2$NHCOBu-t | H | 3-I | 2-Me-4-CF(CF$_3$)$_2$ | 160 |
| 31 | (CH$_2$)$_2$NHCOMe | H | 3-I | 2-Me-4-CF(CF$_3$)$_2$ | 210 |
| 32 | (CH$_2$)$_2$NHCOMe | H | 3-I | 2-Me-4-OCF$_3$ | 210 |
| 33 | CH(Me)CH$_2$NHCOMe | H | 3-I | 2-Me-4-CF(CF$_3$)$_2$ | 140 |
| 34 | CH(Me)CH$_2$NHCOEt | H | 3-I | 2-Me-4-CF(CF$_3$)$_2$ | 230 |
| 35 | C(Me)$_2$CH$_2$NHCOEt | H | 3-I | 2-Me-4-CF(CF$_3$)$_2$ | 220 |
| 36 | CH(Me)CH$_2$NHCOMe | H | 3-I | 2-Me-4-OCF$_3$ | 215 |
| 37 | (CH$_2$)$_2$NHCON(Me)$_2$ | H | 3-I | 2-Me-4-CF(CF$_3$)$_2$ | 170 |
| 38 | CH(Me)CH$_2$NHCON(Me)$_2$ | H | 3-I | 2-Me-4-CF(CF$_3$)$_2$ | 250 |
| 39 | CH(Me)CH$_2$NHSO$_2$Me | H | 3-I | 2-Me-4-CF(CF$_3$)$_2$ | 110 |
| 40 | CH(Me)CH$_2$NHSO$_2$Ph | H | 3-I | 2-Me-4-CF(CF$_3$)$_2$ | 130 |
| 41 | CH(Me)CH$_2$NHSO$_2$Et | H | 3-I | 2-Me-4-CF(CF$_3$)$_2$ | 155 |
| 42 | CH(Me)CH$_2$N(Me)SO$_2$Me | H | 3-I | 2-Me-4-CF(CF$_3$)$_2$ | 100 |
| 43 | CH(Me)CH$_2$N(Me)SO$_2$Me | H | 3-I | 2-Me-4-OCF$_3$ | 200 |
| 44 | CH(Me)CH$_2$N(Me)SO$_2$Me | H | 3-I | H | 250 |
| 45 | CH(Me)CH$_2$NHSO$_2$N(Me)$_2$ | H | 3-I | 2-Me-4-CF(CF$_3$)$_2$ | 95 |
| 46 | (CH$_2$)$_3$N(Me)$_2$ | H | 3-I | 2-Me-4-CF(CF$_3$)$_2$ | 155 |
| 47 | (CH$_2$)$_3$N(Me)$_2$ | H | 3-I | 2-Me-4-OCF$_3$ | 115 |
| 48 | CH(Me)CH$_2$NH—P(=S)(OMe)$_2$ | H | 3-I | 2-Me-4-CF(CF$_3$)$_2$ | 175 |
| 49 | CH(Me)CH$_2$NH—P(=S)(OMe)$_2$ | H | 3-I | 2-Me-4-OCF$_3$ | 125 |
| 50 | CH(Me)CH$_2$NH—P(=S)(OEt)$_2$ | H | 3-I | 2-Me-4-CF(CF$_3$)$_2$ | 180 |
| 51 | CH$_2$—(2,2-Me$_2$-1,3-Dioxolan-4-yl) | H | 3-I | 2-Me-4-CF(CF$_3$)$_2$ | 170 |
| 52 | CH$_2$—(2,2-Me$_2$-1,3-Dioxolan-4-yl) | H | 3-I | 2-Me-4-OCF$_3$ | 165 |
| 53 | CH$_2$—(tetrahydropyran-4-yl) | H | 3-I | 2-Me-4-OCF$_3$ | 176 |
| 54 | CH$_2$—(tetrahydropyran-4-yl) | H | 3-I | 2-Me-4-CF(CF$_3$)$_2$ | 145 |
| 55 | CH$_2$OMe | Et | 3-Cl | 2-Me-4-CF(CF$_3$)$_2$ | 136 |
| 56 | CH(Me)CH$_2$OMe | H | 3-I | 2-Me-4-CF(CF$_3$)$_2$ | 136 |
| 57 | CH(Me)CH$_2$OMe | H | 3-I | 2-Me-4-OCF$_3$ | 137 |
| 58 | CH(Me)CH$_2$OH | H | 3-Cl | 2-Me-4-CF(CF$_3$)$_2$ | 200 |
| 59 | CH(Me)(CH$_2$)$_2$OMe | H | 3-I | 2-Me-4-CF(CF$_3$)$_2$ | 164 |
| 60 | C(Me)$_2$CH$_2$OH | H | 3-I | 2-Me-4-CF(CF$_3$)$_2$ | 210 |
| 61 | C[—(CH$_2$)$_4$—]CH$_2$OH | H | 3-I | 2-Me-4-CF(CF$_3$)$_2$ | 207 |
| 62 | CH(Me)(CH$_2$)$_2$OCH$_2$CF$_3$ | H | 3-I | 2-Me-4-CF(CF$_3$)$_2$ | 191 |

TABLE 1-continued (Z¹ = Z² = O, R³ = H, Q¹~Q⁵ = C, unless otherwise specified.)

| No. | —A¹—B—R¹ | R² | Xn | Ym | Physical property: Melting point ° C. |
|---|---|---|---|---|---|
| 63 | CH(Me)(CH₂)₂OEt | H | 3-I | 2-Me-4-CF(CF₃)₂ | 100 |
| 64 | CH(Me)(CH₂)₂OEt | H | 3-I | 2-Me-4-OCF₃ | 164 |
| 65 | CH(Me)(CH₂)₂OEt | H | 3-I | 2-Cl-4-OCF₃ | 151 |
| 66 | CH(Me)(CH₂)₂O—(CH₂)₂OMe | H | 3-I | 2-Me-4-CF(CF₃)₂ | 71 |
| 67 | CH(Me)CH₂OEt | H | 3-I | 2-Me-4-CF(CF₃)₂ | 171 |
| 68 | CH(Me)CH₂OCH₂Ph | H | 3-I | 2-Me-4-CF(CF₃)₂ | 186 |
| 69 | CH(Me)CH₂OPr | H | 3-I | 2-Me-4-CF(CF₃)₂ | 160 |
| 70 | CH(Me)(CH₂)₂OPr | H | 3-I | 2-Me-4-CF(CF₃)₂ | 146 |
| 71 | CH(Me)CH₂O(CH₂)₂OMe | H | 3-I | 2-Me-4-CF(CF₃)₂ | 153 |
| 72 | CH(Me)CH₂OBu-i | H | 3-I | 2-Me-4-CF(CF₃)₂ | 188 |
| 73 | CH(Me)CH₂OBu-i | H | 3-I | 2-OPh | 113 |
| 74 | CH(Me)(CH₂)₂OBu-i | H | 3-I | 2-Me-4-CF(CF₃)₂ | 158 |
| 75 | CH(Me)(CH₂)₂OBu-i | H | 3-I | 4-Cl | 204 |
| 76 | CH(Me)CH₂O(CH₂)₂SMe | H | 3-I | 2-Me-4-CF(CF₃)₂ | 168 |
| 77 | CH(Me)CH₂O(CH₂)₂SEt | H | 3-I | 2-Me-4-CF(CF₃)₂ | 140 |
| 78 | CH(Me)CH₂OPh | H | 3-I | 2-Me-4-CF(CF₃)₂ | 110 |
| 79 | CH(Me)CH₂OPh | H | 3-I | H | 130 |
| 80 | CH(Me)CH₂OPh | H | H | 2-Me-4-CF(CF₃)₂ | Amorphous |
| 81 | CH(Me)CH₂O(4-Cl-Ph) | H | 3-I | 2-Me-4-CF(CF₃)₂ | 200 |
| 82 | CH(Me)CH₂O(4-Cl-Ph) | H | 3-I | 2,4,6-(Me)₃ | 220 |
| 83 | CH(Me)CH₂O(3-CF₃-Ph) | H | 3-I | 2-Me-4-CF(CF₃)₂ | 100 |
| 84 | CH(Me)CH₂O(3-CF₃-Ph) | H | 3-I | 2-Me-4-OCF₃ | 140 |
| 85 | CH(Me)CH₂OCOMe | H | 3-I | 2-Me-4-CF(CF₃)₂ | 110 |
| 86 | CH(Me)CH₂OCOMe | H | 3-I | 2-Me-4-OCF₃ | 155 |
| 87 | C(Me)₂CH₂OCOMe | H | 3-I | 2-Me-4-CF(CF₃)₂ | 180 |
| 88 | CH(Me)CH₂OCON(Me)₂ | H | 3-I | 2-Me-4-CF(CF₃)₂ | 100 |
| 89 | CH(Me)CH₂OCON(Me)₂ | H | 3-I | 2-Me-4-OCF₃ | 140 |
| 90 | CH(Me)CH₂OCON(Et)₂ | H | 3-I | 2-Me-4-CF(CF₃)₂ | 190 |
| 91 | C(Me)₂CH₂OCON(Me)₂ | H | 3-I | 2-Me-4-CF(CF₃)₂ | 115 |
| 92 | C(Me)₂CH₂OCON(Me)₂ | H | 3-I | 2-Me-4-OCF₃ | 150 |
| 93 | CH(Me)CH₂OCON(Pr-i)₂ | H | 3-I | 2-Me-4-CF(CF₃)₂ | 100 |
| 94 | CH(Me)CH₂OCON(Me)Ph | H | 3-I | 2-Me-4-CF(CF₃)₂ | 105 |
| 95 | CH(Me)CH₂OCO—N(—CH₂CH₂OCH₂CH₂—) | H | 3-I | 2-Me-4-CF(CF₃)₂ | 255 |
| 96 | CH(Me)CH₂OCONHEt | H | 3-I | 2-Me-4-CF(CF₃)₂ | 185 |
| 97 | CH(Me)CH₂OCONHEt | H | 3-I | 2-Me-4-OCF₃ | 220 |
| 98 | CH(Me)CH₂OCO—N(—CH₂CH₂CH₂CH₂—) | H | 3-I | 2-Me-4-CF(CF₃)₂ | Amorphous |
| 99 | CH(Me)CH₂OCONHPr-i | H | 3-I | 2-Me-4-CF(CF₃)₂ | 130 |
| 100 | C(Me)₂CH₂OCONHEt | H | 3-I | 2-Me-4-CF(CF₃)₂ | 225 |
| 101 | CH(Me)CH₂OCONHMe | H | 3-I | 2-Me-4-CF(CF₃)₂ | 190 |
| 102 | CH(Me)CH₂OCONHMe | H | 3-I | 2-Me-4-OCF₃ | 200 |
| 103 | CH(Me)CH₂OCONHPr | H | 3-I | 2-Me-4-CF(CF₃)₂ | 175 |
| 104 | CH(Me)CH₂OCONHPr | H | 3-I | 2-Me-4-OCF₃ | 205 |
| 105 | CH(Me)CH₂OCONHPr-i | H | 3-I | 2-Me-4-CF(CF₃)₂ | 170 |
| 106 | CH(Me)CH₂OCONHPr-i | H | 3-I | 2-Me-4-OCF₃ | 215 |
| 107 | CH(Me)CH₂OCONHCH₂Ph | H | 3-I | 2-Me-4-CF(CF₃)₂ | 175 |
| 108 | CH(Me)CH₂OCONHCH₂Ph | H | 3-I | 2-Me-4-OCF₃ | 190 |
| 109 | CH(Me)CH₂OCONHPh | H | 3-I | 2-Me-4-CF(CF₃)₂ | 190 |
| 110 | CH(Me)CH₂OCONHPh | H | 3-I | 2-Me-4-OCF₃ | 230 |
| 111 | CH(Me)CH₂O—P(=S)(OMe)₂ | H | 3-I | 2-Me-4-CF(CF₃)₂ | 115 |
| 112 | CH(Me)CH₂O—P(=S)(OEt)₂ | H | 3-I | 2-Me-4-CF(CF₃)₂ | 140 |
| 113 | CH(Me)CH₂O—P(=S)(OEt)₂ | H | 3-I | 2-Me-4-OCF₃ | 115 |
| 114 | CH(Me)CH₂O—P(=S)(OEt)₂ | H | 3-I | H | 125 |
| 115 | CH(Me)CH₂O—P(=S)(OEt)₂ | H | 3-I | 2-Me | 95 |
| 116 | C(Me)₂CH₂O—P(=S)(OMe)₂ | H | 3-I | 2-Me-4-CF(CF₃)₂ | 120 |
| 117 | CH(Me)CH₂O—P(=O)(OEt)₂ | H | 3-I | 2-Me-4-CF(CF₃)₂ | Amorphous |
| 118 | CH(Me)CH₂O—P(=O)(OEt)₂ | H | 3-I | H | Amorphous |
| 119 | CH(Me)CH₂OCOCF₃ | H | 3-NO₂ | 2-Me-4-CF(CF₃)₂ | 209 |
| 120 | C(Me)₂CH₂OCOCF₃ | H | 3-I | 2-Me-4-CF(CF₃)₂ | 190 |
| 121 | C(Me)₂CH₂OCOCF₃ | H | 3-I | 2-Cl-4-CF(CF₃)₂ | 150 |
| 122 | C(Me)₂CH₂OCOCF₃ | H | 6-I | 2-Cl-4-CF(CF₃)₂ | 95 |
| 123 | CH(Me)CH₂OCO-Ph | H | 3-I | 2-Me-4-CF(CF₃)₂ | |
| 124 | C(Me)₂CH₂OCO-Ph | H | 3-I | 2-Me-4-CF(CF₃)₂ | |

TABLE 1-continued

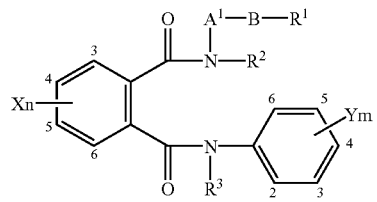

($Z^1 = Z^2 = O$, $R^3 = H$, $Q^1 \sim Q^5 = C$, unless otherwise specified.)

| No. | —$A^1$—B—$R^1$ | $R^2$ | Xn | Ym | Physical property: Melting point ° C. |
|---|---|---|---|---|---|
| 125 | CH(Me)CH$_2$OCO-(3-Pyr) | H | 3-I | 2-Me-4-CF(CF$_3$)$_2$ | |
| 126 | C(Me)$_2$CH$_2$OCO-(3-Pyr) | H | 3-I | 2-Me-4-CF(CF$_3$)$_2$ | |
| 127 | (CH$_2$)$_2$OCONHEt | Me | H | 2-Me-4-CF$_2$CF$_3$ | 52 |
| 128 | (CH$_2$)$_2$OCONHEt | Me | H | 2-Me-4-CF(CF$_3$)$_2$ | 113 |
| 129 | C(Me)$_2$CH$_2$OCONHPr-n | H | 3-I | 2-Me-4-CF(CF$_3$)$_2$ | 220 |
| 130 | C(Me)$_2$CH$_2$OCONHPr-n | H | 3-I | 2-Cl-4-CF(CF$_3$)$_2$ | 200 |
| 131 | CH(Me)CH$_2$OCONHPr-i | H | 3-I | 2-Me-4-CF(CF$_3$)$_2$ | |
| 132 | C(Me)$_2$CH$_2$OCONHPr-i | H | 3-I | 2-Me-4-CF(CF$_3$)$_2$ | |
| 133 | CH(Me)CH$_2$OCONHPr-c | H | 3-I | 2-Me-4-CF(CF$_3$)$_2$ | 114 |
| 134 | CH(Me)CH$_2$OCONHPr-c | H | 3-I | 2-Me-4-OCF$_3$ | 212 |
| 135 | C(Me)$_2$CH$_2$OCONHPr-c | H | H | 2-Me-4-CF(CF$_3$)$_2$ | 176 |
| 136 | C(Me)$_2$CH$_2$OCONHPr-c | H | 3-I | 2-Me-4-CF(CF$_3$)$_2$ | 231 |
| 137 | C(Me)$_2$CH$_2$OCONHBu-n | H | 3-I | 2-Me-4-CF(CF$_3$)$_2$ | |
| 138 | C(Me)$_2$CH$_2$OCONHBu-s | H | 3-I | 2-Me-4-CF(CF$_3$)$_2$ | |
| 139 | CH(Me)CH$_2$OCONHBu-t | H | 3-I | 2-Me-4-CF(CF$_3$)$_2$ | 215 |
| 140 | CH(Me)CH$_2$OCONHBu-t | H | 3-I | 2-Cl-4-CF(CF$_3$)$_2$ | 190 |
| 141 | C(Me)$_2$CH$_2$OCONHBu-c | H | 3-I | 2-Me-4-CF(CF$_3$)$_2$ | |
| 142 | CH(Me)CH$_2$OCONH—CH$_2$C=CH$_2$ | H | 3-I | 2-Me-4-CF(CF$_3$)$_2$ | 189 |
| 143 | C(Me)$_2$CH$_2$OCONH—CH$_2$C=CH$_2$ | H | H | 2-Me-4-CF(CF$_3$)$_2$ | 174 |
| 144 | C(Me)$_2$CH$_2$OCONH—CH$_2$C=CH$_2$ | H | 3-I | 2-Me-4-CF(CF$_3$)$_2$ | 181 |
| 145 | C(Me)$_2$CH$_2$OCONH—CH$_2$C=CH$_2$ | H | 3-I | 2-Me-4-OCF$_3$ | 196 |
| 146 | C(Me)$_2$CH$_2$OCONH—CH$_2$C≡CH | H | 3-I | 2-Me-4-CF(CF$_3$)$_2$ | |
| 147 | C(Me)$_2$CH$_2$OCONH—CH$_2$C≡CH | H | 3-I | 2-Me-4-OCF$_3$ | |
| 148 | CH(Me)CH$_2$OCONHCH$_2$CF$_3$ | H | 3-I | 2-Me-4-CF(CF$_3$)$_2$ | 124 |
| 149 | C(Me)$_2$CH$_2$OCONHCH$_2$CF$_3$ | H | 3-I | 2-Me-4-CF(CF$_3$)$_2$ | 196 |
| 150 | C(Me)$_2$CH$_2$OCONHCH$_2$—COOMe | H | 3-I | 2-Me-4-CF(CF$_3$)$_2$ | |
| 151 | C(Me)$_2$CH$_2$OCONHCH$_2$—CON(Et)$_2$ | H | 3-I | 2-Me-4-CF(CF$_3$)$_2$ | |
| 152 | C(Me)$_2$CH$_2$OCONHCH$_2$-Ph | H | 3-I | 2-Me-4-CF(CF$_3$)$_2$ | 170 |
| 153 | C(Me)$_2$CH$_2$OCONHCH$_2$-Ph | H | 3-I | 2-Cl-4-CF(CF$_3$)$_2$ | 185 |
| 154 | CH(Me)CH$_2$OCON(CH$_3$)—CH$_2$-Ph | H | 3-I | 2-Me-4-CF(CF$_3$)$_2$ | Paste |
| 155 | CH(Me)CH$_2$OCONHCH$_2$-(2-Cl-Ph) | H | 3-I | 2-Me-4-CF(CF$_3$)$_2$ | |
| 156 | CH(Me)CH$_2$OCONHCH$_2$-(3-Cl-Ph) | H | 3-I | 2-Me-4-CF(CF$_3$)$_2$ | |
| 157 | CH(Me)CH$_2$OCONHCH$_2$-(4-Cl-Ph) | H | 3-I | 2-Me-4-CF(CF$_3$)$_2$ | 181 |
| 158 | CH(Me)CH$_2$OCONHCH$_2$-(2-Me-Ph) | H | 3-I | 2-Me-4-CF(CF$_3$)$_2$ | 170 |
| 159 | CH(Me)CH$_2$OCONHCH$_2$-(4-Me-Ph) | H | 3-I | 2-Me-4-CF(CF$_3$)$_2$ | 188 |
| 160 | CH(Me)CH$_2$OCONHCH$_2$-(2-OMe-Ph) | H | 3-I | 2-Me-4-CF(CF$_3$)$_2$ | |
| 161 | CH(Me)CH$_2$OCONHCH$_2$-(4-OMe-Ph) | H | 3-I | 2-Me-4-CF(CF$_3$)$_2$ | 178 |
| 162 | CH(Me)CH$_2$OCONHCH$_2$-(4-CF$_3$-Ph) | H | 3-I | 2-Me-4-CF(CF$_3$)$_2$ | 186 |
| 163 | CH(Me)CH$_2$OCONHCH$_2$-(2-Pyr) | H | 3-I | 2-Me-4-CF(CF$_3$)$_2$ | |
| 164 | CH(Me)CH$_2$OCONHCH$_2$-[2-(3-Cl-5-CF$_3$-Pyr)] | H | 3-I | 2-Me-4-CF(CF$_3$)$_2$ | |
| 165 | CH(Me)CH$_2$OCONHCH$_2$-(3-Pyr) | H | 3-I | 2-Me-4-CF(CF$_3$)$_2$ | 84 |
| 166 | CH(Me)CH$_2$OCONHCH$_2$-[3-(6-Cl-Pyr)] | H | 3-I | 2-Me-4-CF(CF$_3$)$_2$ | |
| 167 | CH(Me)CH$_2$OCONHCH$_2$-(4-Pyr) | H | H | 2-Me-4-CF(CF$_3$)$_2$ | 137 |
| 168 | CH(Me)CH$_2$OCONHCH$_2$-(4-Pyr) | H | 3-I | 2-Me-4-CF(CF$_3$)$_2$ | 140 |
| 169 | CH(Me)CH$_2$OCONHCH$_2$[5-CF$_3$-1,3,4-Triadiazol-2-yl] | H | 3-I | 2-Me-4-CF(CF$_3$)$_2$ | 169 |
| 170 | CH(Me)CH$_2$OCONH(CH$_2$)$_2$—OMe | H | 3-I | 2-Me-4-CF(CF$_3$)$_2$ | Paste |
| 171 | CH(Me)CH$_2$OCONH(CH$_2$)$_2$—OMe | H | 3-I | 2-Me-4-OCF$_3$ | 231 |
| 172 | C(Me)$_2$CH$_2$OCONH(CH$_2$)$_2$—OMe | H | 3-I | 2-Me-4-CF(CF$_3$)$_2$ | 184 |
| 173 | C(Me)$_2$CH$_2$OCONH(CH$_2$)$_2$—OMe | H | 3-I | 2-Me-4-OCF$_3$ | 135 |
| 174 | CH(Me)CH$_2$OCONH(CH$_2$)$_3$—OMe | H | 3-I | 2-Me-4-CF(CF$_3$)$_2$ | |
| 175 | CH(Me)CH$_2$OCONH(CH$_2$)$_3$—OMe | H | 3-I | 2-Me-4-OCF$_3$ | |
| 176 | CH(Me)CH$_2$OCONH(CH$_2$)$_2$—SMe | H | 3-I | 2-Me-4-CF(CF$_3$)$_2$ | |
| 177 | CH(Me)CH$_2$OCONH(CH$_2$)$_2$—SMe | H | 3-I | 2-Me-4-OCF$_3$ | |
| 178 | C(Me)$_2$CH$_2$OCONH(CH$_2$)$_2$—SMe | H | 3-I | 2-Me-4-CF(CF$_3$)$_2$ | |
| 179 | C(Me)$_2$CH$_2$OCONH(CH$_2$)$_2$—SMe | H | 3-I | 2-Me-4-OCF$_3$ | |
| 180 | C(Me)$_2$CH$_2$OCONH(CH$_2$)$_2$—SOMe | H | 3-I | 2-Me-4-CF(CF$_3$)$_2$ | |
| 181 | CH(Me)CH$_2$OCONH(CH$_2$)$_2$—SOMe | H | 3-I | 2-Me-4-OCF$_3$ | |
| 182 | CH(Me)CH$_2$OCONH(CH$_2$)$_3$—SMe | H | 3-I | 2-Me-4-CF(CF$_3$)$_2$ | 171 |
| 183 | CH(Me)CH$_2$OCONH(CH$_2$)$_3$—SMe | H | 3-I | 2-Me-4-OCF$_3$ | 176 |
| 184 | C(Me)$_2$CH$_2$OCONH(CH$_2$)$_3$—SMe | H | 3-I | 2-Me-4-CF(CF$_3$)$_2$ | 95 |
| 185 | C(Me)$_2$CH$_2$OCONH(CH$_2$)$_3$—SMe | H | 3-I | 2-Me-4-OCHF$_2$ | 178 |
| 186 | C(Me)$_2$CH$_2$OCONH(CH$_2$)$_3$—SO$_2$Me | H | 3-I | 2-Me-4-CF(CF$_3$)$_2$ | |

TABLE 1-continued

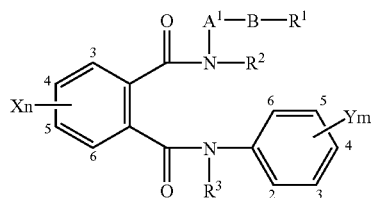

($Z^1 = Z^2 = O$, $R^3 = H$, $Q^1 \sim Q^5 = C$, unless otherwise specified.)

| No. | —$A^1$—B—$R^1$ | $R^2$ | Xn | Ym | Physical property: Melting point ° C. |
|---|---|---|---|---|---|
| 187 | C(Me)$_2$CH$_2$OCONH(CH$_2$)$_3$—SO$_2$Me | H | 3-I | 2-Me-4-OCF$_3$ | |
| 188 | CH(Me)CH$_2$OC(=S)NHEt | H | 3-I | 2-Me-4-CF(CF$_3$)$_2$ | |
| 189 | C(Me)$_2$CH$_2$OC(=S)NHEt | H | 3-I | 2-Me-4-CF(CF$_3$)$_2$ | |
| 190 | CH(Me)CH$_2$OP(=S)—(OMe)$_2$ | H | 3-I | 2-Me-4-OCF$_3$ | |
| 191 | CH(Me)CH$_2$OP(=S)—(OMe)$_2$ | H | H | 2-Me-4-OCF$_3$ | |
| 192 | (CH$_2$)$_3$OCONHEt | H | 3-I | 2-Me-4-CF(CF$_3$)$_2$ | |
| 193 | (CH$_2$)$_3$OCONHEt | H | 3-I | 2-Me-4-OCF$_3$ | |
| 194 | CH(Me)(CH$_2$)$_2$OCONHEt | H | 3-I | 2-Me-4-CF(CF$_3$)$_2$ | 166 |
| 195 | CH(Me)(CH$_2$)$_2$OCO—N(Et)$_2$ | H | 3-I | 2-Me-4-CF(CF$_3$)$_2$ | |
| 196 | CH(Me)(CH$_2$)$_2$OCONH—CH$_2$-Ph | H | 3-I | 2-Me-4-CF(CF$_3$)$_2$ | |
| 197 | C(Me)$_2$(CH$_2$)$_2$OCONHMe | H | 3-I | 2-Me-4-CF(CF$_3$)$_2$ | |
| 198 | (CH$_2$)$_4$OCONHEt | H | 3-I | 2-Me-4-CF(CF$_3$)$_2$ | 76 |
| 199 | (CH$_2$)$_4$OCONHPr-i | H | 3-I | 2-Me-4-CF(CF$_3$)$_2$ | 132 |
| 200 | CH(Me)(CH$_2$)$_3$OCONHEt | H | 3-I | 2-Me-4-CF(CF$_3$)$_2$ | |
| 201 | CH(Me)(CH$_2$)$_3$OCO—N(Et)$_2$ | H | 3-I | 2-Me-4-CF(CF$_3$)$_2$ | |
| 202 | CH(Me)(CH$_2$)$_3$OCONH—CH$_2$-Ph | H | 3-I | 2-Me-4-CF(CF$_3$)$_2$ | |
| 203 | C(Me)$_2$(CH$_2$)$_3$OCONHMe | H | 3-I | 2-Me-4-CF(CF$_3$)$_2$ | |
| 204 | (CH$_2$)$_5$OCONHEt | H | H | 2-Me-4-CF$_2$CF$_3$ | 138 |
| 205 | (CH$_2$)$_5$OCONHEt | H | H | 2-Me-4-CF(CF$_3$)$_2$ | 136 |
| 206 | CH(Me)(CH$_2$)$_4$OCONHEt | H | 3-I | 2-Me-4-CF(CF$_3$)$_2$ | |
| 207 | CH(Me)(CH$_2$)$_4$OCO—N(Et)$_2$ | H | 3-I | 2-Me-4-CF(CF$_3$)$_2$ | |
| 208 | CH(Me)(CH$_2$)$_4$OCONH—CH$_2$-Ph | H | 3-I | 2-Me-4-CF(CF$_3$)$_2$ | |
| 209 | C(Me)$_2$(CH$_2$)$_4$OCONHMe | H | 3-I | 2-Me-4-CF(CF$_3$)$_2$ | |
| 210 | CH(Me)CH$_2$OCONHEt | H | 3-F | 2-Me-4-CF(CF$_3$)$_2$ | 178 |
| 211 | CH(Me)CH$_2$OCONHEt | H | 3-F | 2-Me-4-OCF$_3$ | 179 |
| 212 | CH(Me)CH$_2$OCONHCH$_2$-Ph | H | 3-F | 2-Me-4-CF(CF$_3$)$_2$ | 131 |
| 213 | C(Me)$_2$CH$_2$OCONHMe | H | 3-F | 2-Me-4-CF(CF$_3$)$_2$ | |
| 214 | CH(Me)CH$_2$OCONHEt | H | 3-Cl | 2-Me-4-CF(CF$_3$)$_2$ | 99 |
| 215 | CH(Me)CH$_2$OCONHEt | H | 3-Cl | 2-Me-4-CF$_2$CF$_3$ | 145 |
| 216 | CH(Me)CH$_2$OCONHEt | H | 3-Cl | 2-Me-4-OCHF$_2$ | 188 |
| 217 | CH(Me)CH$_2$OCONHEt | H | 3-Cl | 2-Me-4-OCF$_3$ | |
| 218 | CH(Me)CH$_2$OCONHCH$_2$-Ph | H | 3-Cl | 2-Me-4-CF(CF$_3$)$_2$ | |
| 219 | C(Me)$_2$CH$_2$OCONHMe | H | 3-Cl | 2-Me-4-CF(CF$_3$)$_2$ | |
| 220 | CH(Me)CH$_2$OCONHEt | H | 4-Cl | 2-Me-4-CF(CF$_3$)$_2$ | |
| 221 | CH(Me)CH$_2$OCONHEt | H | 4-Cl | 2-Me-4-OCF$_3$ | |
| 222 | CH(Me)CH$_2$OCONHEt | H | 3-Br | 2-Me-4-CF(CF$_3$)$_2$ | 164 |
| 223 | CH(Me)CH$_2$OCONHEt | H | 3-Br | 2-Me-4-OCF$_3$ | 196 |
| 224 | CH(Me)CH$_2$OCONHCH$_2$-Ph | H | 3-Br | 2-Me-4-CF(CF$_3$)$_2$ | |
| 225 | C(Me)$_2$CH$_2$OCONHMe | H | 3-Br | 2-Me-4-CF(CF$_3$)$_2$ | |
| 226 | CH(Me)CH$_2$OCONHEt | H | 4-I | 2-Me-4-CF(CF$_3$)$_2$ | |
| 227 | CH(Me)CH$_2$OCONHEt | H | 4-I | 2-Me-4-OCF$_3$ | |
| 228 | CH(Me)CH$_2$OCONHEt | H | 3,4-Cl$_2$ | 2-Me-4-CF(CF$_3$)$_2$ | |
| 229 | CH(Me)CH$_2$OCONHCH$_2$-Ph | H | 3,4-Cl$_2$ | 2-Me-4-CF(CF$_3$)$_2$ | 139 |
| 230 | CH(Me)CH$_2$OCONHEt | H | 3,4-Cl$_2$ | 2-Me-4-OCF$_3$ | 193 |
| 231 | CH(Me)CH$_2$OCONHEt | H | 3-Br-4-Cl | 2-Me-4-CF(CF$_3$)$_2$ | |
| 232 | CH(Me)CH$_2$OCONHEt | H | 3,4-Br$_2$ | 2-Me-4-CF(CF$_3$)$_2$ | |
| 233 | CH(Me)CH$_2$OCONHEt | H | 3-I-4-Cl | 2-Me-4-CF(CF$_3$)$_2$ | |
| 234 | CH(Me)CH$_2$OCONHEt | H | 3,4-I$_2$ | 2-Me-4-CF(CF$_3$)$_2$ | |
| 235 | CH(Me)CH$_2$OCONHEt | H | 3-NO$_2$ | 2-Me-4-CF(CF$_3$)$_2$ | 194 |
| 236 | CH(Me)CH$_2$OCONHCH$_2$-Ph | H | 3-NO$_2$ | 2-Me-4-OCF$_3$ | 151 |
| 237 | CH(Me)CH$_2$OCON(Et)$_2$ | H | 3-NO$_2$ | 2-Me-4-CF(CF$_3$)$_2$ | |
| 238 | C(Me)$_2$CH$_2$OCONHMe | H | 3-NO$_2$ | 2-Me-4-CF(CF$_3$)$_2$ | |
| 239 | CH(Me)CH$_2$OCONHEt | H | 3-CF$_3$ | 2-Me-4-CF(CF$_3$)$_2$ | |
| 240 | CH(Me)CH$_2$OCONHCH$_2$-Ph | H | 3-CF$_3$ | 2-Me-4-OCF$_3$ | |
| 241 | CH(Me)CH$_2$OCON(Et)$_2$ | H | 3-CF$_3$ | 2-Me-4-CF(CF$_3$)$_2$ | 178 |
| 242 | C(Me)$_2$CH$_2$OCONHMe | H | 3-CF$_3$ | 2-Me-4-OCF$_3$ | |

TABLE 1-continued

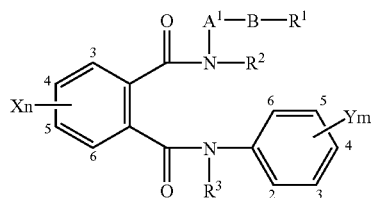

($Z^1 = Z^2 = O$, $R^3 = H$, $Q^1 \sim Q^5 = C$, unless otherwise specified.)

| No. | —$A^1$—B—$R^1$ | $R^2$ | Xn | Ym | Physical property: Melting point ° C. |
|---|---|---|---|---|---|
| 243 | CH(Me)CH$_2$OCONHEt | H | 4-CF$_3$ | 2-Me-4-CF(CF$_3$)$_2$ | 203 |
| 244 | CH(Me)CH$_2$OCONHEt | H | 3-OCF$_3$ | 2-Me-4-OCF$_3$ | |
| 245 | CH(Me)CH$_2$OCONHCH$_2$-Ph | H | 3-OCF$_3$ | 2-Me-4-CF(CF$_3$)$_2$ | |
| 246 | CH(Me)CH$_2$OCON(Et)$_2$ | H | 3-OCF$_3$ | 2-Me-4-OCF$_3$ | |
| 247 | C(Me)$_2$CH$_2$OCONHMe | H | 3-OCF$_3$ | 2-Me-4-CF(CF$_3$)$_2$ | 182 |
| 248 | CH(Me)CH$_2$OCONHEt | H | 3-SMe | 2-Me-4-CF(CF$_3$)$_2$ | |
| 249 | CH(Me)CH$_2$OCONHEt | H | 3-SOMe | 2-Me-4-CF(CF$_3$)$_2$ | |
| 250 | CH(Me)CH$_2$OCONHEt | H | 3-SO$_2$Me | 2-Me-4-CF(CF$_3$)$_2$ | |
| 251 | CH(Me)CH$_2$OCONHEt | H | 3-SCF$_3$ | 2-Me-4-CF(CF$_3$)$_2$ | |
| 252 | CH(Me)CH$_2$OCONHEt | H | 3-SOCF$_3$ | 2-Me-4-CF(CF$_3$)$_2$ | |
| 253 | CH(Me)CH$_2$OCONHEt | H | 3-SO$_2$CF$_3$ | 2-Me-4-CF(CF$_3$)$_2$ | |
| 254 | CH(Me)CH$_2$OCONHEt | H | 3-C≡CH | 2-Me-4-CF(CF$_3$)$_2$ | |
| 255 | CH(Me)CH$_2$OCONHEt | H | 3-C≡C-Bu-t | 2-Me-4-OCF$_3$ | |
| 256 | CH(Me)CH$_2$OCONHEt | H | 3-C≡C-Ph | 2-Me-4-CF(CF$_3$)$_2$ | |
| 257 | CH(Me)CH$_2$OCONHEt | H | 3-C≡C—CF$_3$ | 2-Me-4-OCF$_3$ | |
| 258 | CH(Me)CH$_2$OCONHEt | H | 3-C≡C—Si—(Me)$_3$ | 2-Me-4-CF(CF$_3$)$_2$ | |
| 259 | CH(Me)CH$_2$OCONHEt | H | 3-CH=CH—CH=CH-4 | 2-Me-4-CF(CF$_3$)$_2$ | 207 |
| 260 | CH(Me)CH$_2$OCONHEt | H | 3-CH=CH—CH=CH-4 | 2-Me-4-OCF$_3$ | 185 |
| 261 | CH(Me)CH$_2$OCONHEt | H | 3-OCF$_2$—O-4 | 2-Me-4-CF(CF$_3$)$_2$ | |
| 262 | CH(Me)CH$_2$OCONHEt | H | 3-OCF$_2$—CF$_2$O-4 | 2-Me-4-CF(CF$_3$)$_2$ | |
| 263 | CH(Me)CH$_2$OCONHEt | H | 3-I | 2-Me-4-Cl | 202 |
| 264 | CH(Me)CH$_2$OCONHEt | H | 3-I | 2-Me-4-Cl ($R^3$ = Me) | Paste |
| 265 | CH(Me)CH$_2$OCONHEt | H | 3-I | 2-Me-4-CF$_3$ | 217 |
| 266 | CH(Me)CH$_2$OCONHEt | H | 3-I | 2-Cl-4-CF$_3$ | 208 |
| 267 | CH(Me)CH$_2$OCONHEt | H | 3-I | 2-Me-4-CF$_2$CF$_3$ | 163 |
| 268 | CH(Me)CH$_2$OCONHCH$_2$-Ph | H | 3-I | 2-Me-4-CF$_2$CF$_3$ | 168 |
| 269 | CH(Me)CH$_2$OCONHEt | H | 3-I | 2-Et-4-CF$_2$CF$_3$ | 179 |
| 270 | CH(Me)CH$_2$OCONHEt | H | 3-I | 2-F-4-CF$_2$CF$_3$ | 176 |
| 271 | CH(Me)CH$_2$OCONHEt | H | 3-I | 2-Cl-4-CF$_2$CF$_3$ | 184 |
| 272 | CH(Me)CH$_2$OCONHEt | H | 3-I | 2-Me-4-C$_3$F$_7$-n | 173 |
| 273 | CH(Me)CH$_2$OCONHEt | H | 3-I | 2-Me-4-C$_4$F$_9$-n | |
| 274 | C(Me)$_2$CH$_2$OCONHMe | H | 3-I | 2-Cl-4-CF(CF$_3$)$_2$ | 140 |
| 275 | CH(Me)CH$_2$OCONHEt | H | 3-I | 2-OMe-4-CF(CF$_3$)$_2$ | 168 |
| 276 | CH(Me)CH$_2$OCONHEt | H | 3-I | 2-Me-4-CF(CF$_3$)—CF$_2$CF$_3$ | |
| 277 | CH(Me)CH$_2$OCONHEt | H | 3-I | 2-Me-3-F-4-CF(CF$_3$)$_2$ | |
| 278 | CH(Me)CH$_2$OCONHEt | H | 3-I | 2-Me-3-OMe-4-CF(CF$_3$)$_2$ | 139 |
| 279 | CH(Me)CH$_2$OCONHEt | H | 3-I | 2-Me-4-C(CF$_3$)$_2$—OEt | 193 |
| 280 | CH(Me)CH$_2$OCONHEt | H | 3-I | 2-Br-4-OCF$_3$ | 189 |
| 281 | CH(Me)CH$_2$OCONHEt | H | 3-I | 2-Cl-4-OCF$_3$ | |
| 282 | CH(Me)CH$_2$OCONHEt | H | 3-I | 2-Me-4-OCF$_2$CF$_3$ | |
| 283 | CH(Me)CH$_2$OCONHEt | H | 3-I | 2-Me-4-OC$_3$F$_7$-n | |
| 284 | CH(Me)CH$_2$OCONHEt | H | 3-I | 2-Me-4-OCHF$_2$ | 185 |
| 285 | CH(Me)CH$_2$OCONHCH$_2$-Ph | H | H | 2-Me-4-OCF$_2$CHF$_2$ | 141 |
| 286 | CH(Me)CH$_2$OCONHEt | H | 3-I | 2-Me-4-OCF$_2$CHClF | 193 |

TABLE 1-continued

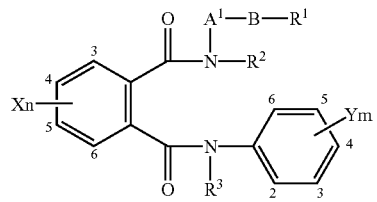

($Z^1$ = $Z^2$ = O, $R^3$ = H, $Q^1$~$Q^5$ = C, unless otherwise specified.)

| No. | —$A^1$—B—$R^1$ | $R^2$ | Xn | Ym | Physical property: Melting point °C. |
|---|---|---|---|---|---|
| 287 | CH(Me)CH$_2$OCONHEt | H | 3-I | 2-Me-4-OCF$_2$CHF—CF$_3$ | 182 |
| 288 | CH(Me)CH$_2$OCONHEt | H | 3-I | 2-Me-4-OCF$_2$CHF—OCF$_3$ | 168 |
| 289 | CH(Me)CH$_2$OCONHEt | H | 3-I | 2-Me-4-O-(3-Cl-5-CF$_3$-Pyr-2-yl) | 200 |
| 290 | CH(Me)CH$_2$OCONHEt | H | 3-I | 2-Me-4-SCF$_3$ | 203 |
| 291 | CH(Me)CH$_2$OCONHEt | H | 3-I | 2-Me-4-SOCF$_3$ | |
| 292 | CH(Me)CH$_2$OCONHEt | H | 3-I | 2-Me-4-SO$_2$CF$_3$ | |
| 293 | CH(Me)CH$_2$OCONHCH$_2$-Ph | H | H | 3-OCF$_2$O-4 | 142 |
| 294 | CH(Me)CH$_2$OCONHEt | H | 3-I | 3-OCF$_2$O-4 | |
| 295 | CH(Me)CH$_2$OCONHEt | H | 3-I | 2-Me-3-OCF$_2$O-4 | |
| 296 | CH(Me)CH$_2$OCONHEt | H | 3-I | 2-Cl-3-OCF$_2$O-4 | |
| 297 | CH(Me)CH$_2$OCONHEt | H | H | 3-OCF$_2$CF$_2$O-4 | 112 |
| 298 | CH(Me)CH$_2$OCONHEt | H | 3-I | 3-CF$_2$CF$_2$O-4 | |
| 299 | CH(Me)CH$_2$OCONHEt | H | 3-I | 3-OCF$_2$CF$_2$-4 | |
| 300 | CH(Me)CH$_2$OCONHEt | H | 3-I | 3-CF$_2$CF$_2$CF$_2$-4 | |
| 301 | CH(Me)CH$_2$OCONHEt | H | 3-I | 3-CF$_2$CF$_2$CF$_2$CF$_2$-4 | |
| 302 | CH(Me)CH$_2$NHCHO | H | 3-I | 2-Me-4-CF(CF$_3$)$_2$ | |
| 303 | C(Me)$_2$CH$_2$NHCHO | H | 3-I | 2-Me-4-CF(CF$_3$)$_2$ | |
| 304 | CH(Me)(CH$_2$)$_2$NHCHO | H | 3-I | 2-Me-4-CF(CF$_3$)$_2$ | |
| 305 | C(Me)$_2$(CH$_2$)$_2$NHCHO | H | 3-I | 2-Me-4-CF(CF$_3$)$_2$ | |
| 306 | CH(Me)CH$_2$NHCOCF$_3$ | H | 3-I | 2-Me-4-CF(CF$_3$)$_2$ | |
| 307 | C(Me)$_2$CH$_2$NHCOCF$_3$ | H | 3-I | 2-Me-4-CF(CF$_3$)$_2$ | |
| 308 | C(Me)$_2$CH$_2$NHCOCF$_3$ | H | 3-I | 2-Me-4-OCF$_3$ | |
| 309 | (CH$_2$)$_2$NHCOMe | Me | H | 2-Me-4-CF(CF$_3$)$_2$ | 108 |
| 310 | (CH$_2$)$_2$NHCOCH$_2$-Ph | Me | H | 2-Me-4-CF(CF$_3$)$_2$ | |
| 311 | (CH$_2$)$_2$NHCO-Ph | Me | H | 2-Me-4-CF(CF$_3$)$_2$ | 191 |
| 312 | CH(Me)CH$_2$NHC(=S)NHEt | H | H | 2-Me-4-CF(CF$_3$)$_2$ | 185 |
| 313 | C(Me)$_2$CH$_2$NHSO$_2$CF$_3$ | H | 3-I | 2-Me-4-CF(CF$_3$)$_2$ | |
| 314 | CH(Me)CH$_2$NHSO$_2$CF$_3$ | H | 3-I | 2-Me-4-CF(CF$_3$)$_2$ | |
| 315 | C(Me)$_2$CH$_2$NHSO$_2$-Ph | H | 3-I | 2-Me-4-CF(CF$_3$)$_2$ | |
| 316 | CH(Me)CH$_2$NHSO$_2$-Ph | H | 3-I | 2-Me-4-CF(CF$_3$)$_2$ | |
| 317 | CH(Me)CH$_2$NH(Me)SO$_2$Me | H | 3-I | 2-Cl-4-CF(CF$_3$)$_2$ | 190 |
| 318 | (CH$_2$)$_2$N(Me)OMe | H | 3-I | 2-Me-4-CF(CF$_3$)$_2$ | 80 |
| 319 | (CH$_2$)$_3$N(Me)OMe | H | 3-I | 2-Me-4-CF(CF$_3$)$_2$ | 91 |
| 320 | (CH$_2$)$_3$N(Me)OMe | H | 3-I | 2-Me-4-OCF$_3$ | 154 |
| 321 | (CH$_2$)$_2$NHCOMe | Me | H | 2-Me-4-CF(CF$_3$)$_2$ | 187 |
| 322 | C(Me)$_2$CH$_2$OCONHMe | H | 3-I | 2-Me-4-CF(CF$_3$)$_2$ | 180 |

Note:
In the table, Q denotes the following group:

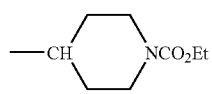

TABLE 2

($Z^1 = Z^2 = O$, $R^2 = R^3 = H$)

| No | —$A^1$—B—$R^1$ | $Q^1$ | $Q^2$ | $Q^3$ | $Q^4$ | $Q^5$ | Xn | Ym | Melting point °C. |
|---|---|---|---|---|---|---|---|---|---|
| 2-1 | CH(Me)CH$_2$OCONHEt | N | C | C | C | C | 3-Cl | 2-Me-4-OCF$_3$ | |
| 2-2 | CH(Me)CH$_2$OCON(Et)$_2$ | N | C | C | C | C | 3-Cl | 2-Me-4-CF$_2$CF$_3$ | |
| 2-3 | CH(Me)CH$_2$OCONHCH$_2$Ph | N | C | C | C | C | 3-Cl | 2-Me-4-CF$_2$CF$_3$ | 85 |
| 2-4 | C(Me)$_2$CH$_2$OCONHMe | N | C | C | C | C | 3-Cl | 2-Me-4-CF(CF$_3$)$_2$ | |
| 2-5 | CH(Me)CH$_2$OCONHEt | C | N | C | C | C | H | 2-Me-4-CF(CF$_3$)$_2$ | 100 |
| 2-6 | CH(Me)CH$_2$OCON(Et)$_2$ | C | N | C | C | C | 3-Br | 2-Me-4-CF$_3$ | |
| 2-7 | CH(Me)CH$_2$OCONHCH$_2$Ph | C | N | C | C | C | H | 2-Cl-4-OCF$_3$ | |
| 2-8 | C(Me)$_2$CH$_2$OCONHMe | C | N | C | C | C | H | 2-Me-4-CF$_2$CF$_3$ | |
| 2-9 | CH(Me)CH$_2$OCONHEt | C | C | N | C | C | H | 2-Me-4-OCF$_3$ | |
| 2-10 | CH(Me)CH$_2$OCON(Et)$_2$ | C | C | N | C | C | H | 2-Me-4-CF$_2$CF$_3$ | |
| 2-11 | CH(Me)CH$_2$OCONHCH$_2$Ph | C | C | N | C | C | H | 2-Me-4-CF(CF$_3$)$_2$ | 94 |
| 2-12 | C(Me)$_2$CH$_2$OCONHMe | C | C | N | C | C | H | 2-Et-4-CF(CF$_3$)$_2$ | |
| 2-13 | CH(Me)CH$_2$OCONHEt | C | C | C | N | C | H | 2-Me-4-CF(CF$_3$)$_2$ | 103 |
| 2-14 | CH(Me)CH$_2$OCON(Et)$_2$ | C | C | C | N | C | H | 2-Cl-4-CF$_3$ | |
| 2-15 | CH(Me)CH$_2$OCONHCH$_2$Ph | C | C | C | N | C | H | 2-Me-4-OCF$_3$ | |
| 2-16 | C(Me)$_2$CH$_2$OCONHMe | C | C | C | N | C | 3-I | 2-Me-4-CF$_2$CF$_3$ | |
| 2-17 | CH(Me)CH$_2$OCONHEt | N | C | N | C | C | H | 2-Me-4-OCF$_3$ | |
| 2-18 | CH(Me)CH$_2$OCON(Et)$_2$ | N | C | C | N | C | H | 2-Me-4-CF$_2$CF$_3$ | |
| 2-19 | C(Me)$_2$CH$_2$OCONHMe | C | N | C | N | C | H | 2-Me-4-CF(CF$_3$)$_2$ | |
| 2-20 | CH(Me)CH$_2$OCONHEt | C | C | C | C | N | 3-I | 2-Me-4-CF$_3$ | |
| 2-21 | CH(Me)CH$_2$OCON(Et)$_2$ | C | C | C | C | N | 3-I | 2-Cl-4-CF$_3$ | |
| 2-22 | CH(Me)CH$_2$OCONHCH$_2$Ph | C | C | C | C | N | 3-I | 2-Me-4-OCF$_3$ | |
| 2-23 | C(Me)$_2$CH$_2$OCONHMe | C | C | C | C | N | 3-I | 2-Cl-4-OCF$_3$ | |
| 2-24 | CH(Me)CH$_2$OCONHEt | C | C | C | C | N | 3-I | 4-CF$_2$CF$_3$ | |
| 2-25 | CH(Me)CH$_2$OCON(Et)$_2$ | C | C | C | C | N | 3-I | 2-Me-4-CF$_2$CF$_3$ | |
| 2-26 | CH(Me)CH$_2$OCONHCH$_2$Ph | C | C | C | C | N | 3-I | 2-Cl-4-CF$_2$CF$_3$ | |
| 2-27 | C(Me)$_2$CH$_2$OCONHMe | C | C | C | C | N | 3-I | 2-OMe-4-CF$_2$CF$_3$ | |
| 2-28 | CH(Me)CH$_2$OCON(Et)$_2$ | C | C | C | C | N | 3-I | 4-CF(CF$_3$)$_2$ | 97 |
| 2-29 | CH(Me)CH$_2$OCON(Et)$_2$ | C | C | C | C | N | 6-I | 4-CF(CF$_3$)$_2$ | 119 |
| 2-30 | CH(Me)CH$_2$OCONHEt | C | C | C | C | N | 3-Cl | 2-Me-4-CF(CF$_3$)$_2$ | |
| 2-31 | CH(Me)CH$_2$OCONHEt | C | C | C | C | N | 3-Br | 2-Me-4-CF(CF$_3$)$_2$ | |
| 2-32 | CH(Me)CH$_2$OCON(Et)$_2$ | C | C | C | C | N | 3-I | 2-Me-4-CF(CF$_3$)$_2$ | 204 |
| 2-33 | CH(Me)CH$_2$OCON(Et)$_2$ | C | C | C | C | N | 6-I | 2-Me-4-CF(CF$_3$)$_2$ | 140 |
| 2-34 | CH(Me)CH$_2$OCONHCH$_2$Ph | C | C | C | C | N | 3-I | 2-Me-4-CF(CF$_3$)$_2$ | |
| 2-35 | C(Me)$_2$CH$_2$OCONHMe | C | C | C | C | N | 3-I | 2-Me-4-CF(CF$_3$)$_2$ | 176 |
| 2-36 | CH(Me)CH$_2$NHCO$_2$Et | C | C | C | C | N | 3-I | 2-Me-4-CF(CF$_3$)$_2$ | |
| 2-37 | CH(Me)CH$_2$NHCOEt | C | C | C | C | N | 3-I | 2-Me-4-CF(CF$_3$)$_2$ | |
| 2-38 | CH(Me)CH$_2$NHSO$_2$Et | C | C | C | C | N | 3-I | 2-Me-4-CF(CF$_3$)$_2$ | |
| 2-39 | CH(Me)CH$_2$OCONHEt | C | C | C | C | N | 3-I | 2-Cl-4-CF(CF$_3$)$_2$ | 188 |
| 2-40 | CH(Me)CH$_2$OCON(Et)$_2$ | C | C | C | C | N | 3-I | 2-Cl-4-CF(CF$_3$)$_2$ | |
| 2-41 | CH(Me)CH$_2$OCONHCH$_2$Ph | C | C | C | C | N | 3-I | 2-Cl-4-CF(CF$_3$)$_2$ | |
| 2-42 | C(Me)$_2$CH$_2$OCONHMe | C | C | C | C | N | 3-I | 2-Cl-4-CF(CF$_3$)$_2$ | |
| 2-43 | CH(Me)CH$_2$OCONHEt | C | C | C | C | N | 3-I | 2-OMe-4-CF(CF$_3$)$_2$ | |
| 2-44 | CH(Me)CH$_2$OCON(Et)$_2$ | C | C | C | C | N | 3-I | 2-OMe-4-CF(CF$_3$)$_2$ | |
| 2-45 | CH(Me)CH$_2$OCONHCH$_2$Ph | C | C | C | C | N | 3-I | 2-OMe-4-CF(CF$_3$)$_2$ | |
| 2-46 | C(Me)$_2$CH$_2$OCONHMe | C | C | C | C | N | 3-I | 2-OMe-4-CF(CF$_3$)$_2$ | |
| 2-47 | CH(Me)CH$_2$OCONHEt | C | C | C | C | N | 3-I | 2-Me-4-OCH(CF$_3$)$_2$ | 197 |
| 2-48 | CH(Me)CH$_2$OCON(Et)$_2$ | C | C | C | C | N | H | 2-Me-4-OCH(CF$_3$)$_2$ | 168 |
| 2-49 | CH(Me)CH$_2$OCON(Et)$_2$ | C | C | C | C | N | 3-I | 2-Me-4-OCH(CF$_3$)$_2$ | 226 |
| 2-50 | CH(Me)CH$_2$OCONHCH$_2$Ph | C | C | C | C | N | 3-I | 2-Me-4-OCH(CF$_3$)$_2$ | 210 |
| 2-51 | C(Me)$_2$CH$_2$OCONHMe | C | C | C | C | N | 3-I | 2-Me-4-OCH(CF$_3$)$_2$ | 213 |
| 2-52 | C(Me)$_2$CH$_2$OCONHMe | C | C | C | C | N | 6-I | 2-Me-4-OCH(CF$_3$)$_2$ | 222 |
| 2-53 | CH(Me)CH$_2$NHCO$_2$Me | C | C | C | C | N | 3-I | 2-Me-4-OCH(CF$_3$)$_2$ | |
| 2-54 | CH(Me)CH$_2$NHCOMe | C | C | C | C | N | 3-I | 2-Me-4-OCH(CF$_3$)$_2$ | |
| 2-55 | CH(Me)CH$_2$NHSO$_2$N(Me)$_2$ | C | C | C | C | N | 3-I | 2-Me-4-OCH(CF$_3$)$_2$ | |
| 2-56 | CH(Me)CH$_2$OCONHMe | C | C | C | C | N | 3-I | 2-Me-4-OCHF$_2$ | |
| 2-57 | CH(Me)CH$_2$OCON(Et)$_2$ | C | C | C | C | N | 3-I | 2-Me-4-OCHF$_2$ | |
| 2-58 | CH(Me)CH$_2$OCONHCH$_2$Ph | C | C | C | C | N | 3-I | 2-Me-4-OCHF$_2$ | |
| 2-59 | C(Me)$_2$CH$_2$OCONHMe | C | C | C | C | N | 3-I | 2-Me-4-OCF$_2$CHF$_2$ | |
| 2-60 | CH(Me)CH$_2$OCONHEt | C | C | C | C | N | 3-I | 2-Me-4-OCF$_2$CHF$_2$ | |
| 2-61 | CH(Me)CH$_2$OCON(Et)$_2$ | C | C | C | C | N | 3-I | 2-Me-4-OCF$_2$CHF$_2$ | |
| 2-62 | CH(Me)CH$_2$OCONHCH$_2$Ph | C | C | C | C | N | 3-I | 2-Me-4-OCF$_2$CHFCF$_3$ | |
| 2-63 | C(Me)$_2$CH$_2$OCONHMe | C | C | C | C | N | 3-I | 2-Me-4-OCF$_2$CHFCF$_3$ | |

TABLE 2-continued

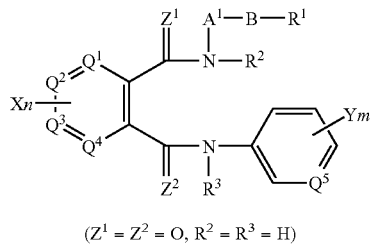

($Z^1 = Z^2 = O$, $R^2 = R^3 = H$)

| No | —$A^1$—B—$R^1$ | $Q^1$ | $Q^2$ | $Q^3$ | $Q^4$ | $Q^5$ | Xn | Ym | Melting point ° C. |
|---|---|---|---|---|---|---|---|---|---|
| 2-64 | CH(Me)CH$_2$OCONHEt | C | C | C | C | N | 3-I | 2-Me-4-OCF$_2$CHFCF$_3$ | |
| 2-65 | CH(Me)CH$_2$OCON(Et)$_2$ | C | C | C | C | N | 3-I | 2-Me-4-OCF$_2$CHFCF$_3$ | |
| 2-66 | CH(Me)CH$_2$OCONHCH$_2$Ph | C | C | C | C | N | 3-I | 2-Me-4-OCF$_2$CHFCF$_3$ | |
| 2-67 | C(Me)$_2$CH$_2$OCONHMe | C | C | C | C | N | 3-I | 2-Me-4-OCF$_2$CHFCF$_3$ | |
| 2-68 | CH(Me)CH$_2$OCONHEt | N | C | C | C | N | 3-I | 2-Me-4-OCF$_2$ | |
| 2-69 | CH(Me)CH$_2$OCON(Et)$_2$ | C | N | C | C | N | 3-I | 2-Me-4-CF$_2$CF$_3$ | |
| 2-70 | CH(Me)CH$_2$OCONHCH$_2$Ph | C | C | N | C | N | 3-I | 2-Me-4-CF(CF$_3$)$_2$ | |
| 2-71 | C(Me)$_2$CH$_2$OCONHMe | C | C | C | N | N | 3-I | 2-Cl-4-CF(CF$_3$)$_2$ | |
| 2-72 | CH(Me)CH$_2$OCONH—CH$_2$(4-(OMe)-Ph) | C | C | C | C | N | 3-I | 2-Me-4-OCH(CF$_3$)$_2$ | 201 |
| 2-73 | CH(Me)CH$_2$OP(=S)—(OMe)$_2$ | C | C | C | C | N | 3-I | 2-Me-4-OCH(CF$_3$)$_2$ | 157 |
| 2-74 | CH(Me)CH$_2$OP(=S)—(OMe)$_2$ | C | C | C | C | N | 6-I | 2-Me-4-OCH(CF$_3$)$_2$ | 134 |

Table 3 shows $^1$H-NMR data of compounds having a physical property expressed by the word "amorphous" in Table 1.

TABLE 3

| No. | $^1$H-NMR [CDCl$_3$/TMS, δ values (ppm)] |
|---|---|
| 80 | 1.33 (d, 3H), 2.37 (s, 3H), 3.91 (dd, 1H), 3.96 (dd, 1H), 4.55 (m, 1H), 6.32 (d, 1H), 6.78 (d, 2H), 6.94(dd, 1H), 7.22 (m, 3H), 7.39 (d, 1H), 7.41 (s, 1H), 7.81 (d, 1H), 7.99 (d, 1H), 8.21 (d, 1H), 8.41 (s, 1H). |
| 98 | 1.17 (d, 3H), 1.75–1.90 (m, 4H), 2.40 (s, 3H), 3.10–3.42 (m, 4H), 4.02 (dd, 1H), 4.22 (dd, 1H), 4.32 (m, 1H), 6.89 (d, 1H), 7.22 (dd, 1H), 7.42 (s, 1H), 7.44 (d, 1H), 7.81 (d, 1H), 7.97 (d, 1H), 8.34(d, 1H), 8.48 (s, 1H). |
| 117 | 1.26 (dt, 6H), 1.28 (d, 3H), 2.38 (s, 3H), 4.08 (m, 6H), 4.39 (s, 1H), 6.79 (d, 1H), 7.23 (dd, 1H), 7.41 (s, 1H), 7.43 (d, 1H), 7.81 (d, 1H), 7.99 (d, 1H), 8.31 (d, 1H), 8.42 (s, 1H). |

Agricultural and horticultural chemicals, in particular, agricultural and horticultural insecticides, which contain as an active ingredient the aromatic diamide derivative of the general formula (I) or salt thereof of the present invention are suitable for controlling various insect pests such as agricultural insect pests, forest insect pests, horticultural insect pests, stored grain insect pests, sanitary insect pests, nematodes, etc., which are injurious to paddy rice, fruit trees, vegetables, other crops, flowers and ornamental plants, and the like. They have a powerful insecticidal effect, for example, on LEPIDOPTERA including summer fruit tortrix (*Adoxophyes orana* fasciata), smaller tea tortrix (*Adoxophyes* sp.), Manchurian fruit moth (*Grapholita inopinata*), oriental fruit moth (*Grapholita molesta*), soybean pod borer (*Leguminivora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae* crucivora), tabacco budworm (*Heliothis* sp.), codling moth (*Laspey resia* pomonella), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), etc.; COLEOPTERA including root-lesion nematode (*Pratylenchus* sp.), soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiocto*-punctata), adzuki bean weevil (*Callosobruchus chinensis*), vegetable weevil (*Listroderes costirostris*), maize weevil (*Sitophilus zeamais*), boll weevil (*Anthonomus gradis* gradis), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican beetle (*Epilachna varivestis*), corn rootworm (*Diabrotica* sp.), etc.; DIPTEPA including melon fly (*Dacus* (*Zeugodacus*) cucurbitae), oriental fruit fly (*Dacus* (*Bactrocera*) *dorsalis*), rice leafminer (*Agromyza oryzae*), onion maggot (*Delia antiqua*), seedcorn maggot (*Delia platura*), soybean pod gall midge (Asphondylia sp.), muscid fly (*Musca domestica*), house mosquito (*Culex pipiens* pipiens), etc.; and TYLENCHIDA including coffee root-lesion nematode (*Pratylenchus coffeae*), potato cyst nematode (*Globodera rostochiensis*), rootknot nematode (*Meloidogyne* sp.), citrus nematode (*Tylenchulus semipenetrans*), *Aphelenchus* sp. (*Aphelenchus avenae*), chrysanthemum foliar nematode (*Aphelenchoides ritzemabosi*), etc.

The agricultural and horticultural chemical, in particular, agricultural and horticultural insecticide, which contains as an active ingredient the aromatic diamide derivative of the general formula (I) or salt thereof of the present invention has a marked insecticidal effect on the above-exemplified insect pests injurious to paddy field crops, upland crops, fruit trees, vegetables, other crops, flowers and ornamental plants, and the like. Therefore, the desired effect of the agricultural and horticultural chemical, in particular, agricultural and horticultural insecticide of the present invention can be obtained by applying the agricultural and horticultural chemical to the paddy field water, stalks and leaves of fruit trees, vegetables, other crops, flowers and ornamental plants, soil, etc., at a season at which the insect pests are expected to appear, before their appearance or at the time when their appearance is confirmed.

The agricultural and horticultural chemical of the present invention is generally prepared into conveniently usable forms according to an ordinary manner for preparation of agrochemicals.

That is, the aromatic diamide derivative of the general formula (I) or a salt thereof and, optionally, an adjuvant are blended with a suitable inert carrier in a proper proportion and prepared into a suitable preparation form such as a suspension, emulsifiable concentrate, soluble concentrate, wettable powder, granules, dust, tablets or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, chemical fertilizers (e.g. ammonium sulfate, ammonium phosphate, ammonium nitrate, urea and ammonium chloride), and compost. These carriers may be used alone or as a mixture thereof.

A material usable as the liquid carrier is selected from materials that have solubility in themselves or which are without such solubility but are capable of dispersing an active ingredient with the aid of an adjuvant. The following are typical examples of the liquid carrier and can be used alone or as a mixture thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbon (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination is some cases, or need not to be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly (vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products.

Adjuvants such as silicone oils may also be used as a defoaming agent.

The content of the compound as active ingredient may be varied as required, and the compound as active ingredient may be used in a proportion properly chosen in the range of 0.01 to 90 parts by weight per 100 parts of the agricultural and horticultural insecticide. For example, in dusts or granules, the suitable content of the compound as active ingredient is from 0.01 to 50% by weight. In emulsifiable concentrates or flowable wettable powders, it is also from 0.01 to 50% by weight.

The agricultural and horticultural chemical, in particular, agricultural and horticultural insecticide of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agricultural and horticultural insecticide of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient)per 10 ares depending upon purposes.

The agricultural and horticultural chemical, in particular, agricultural and horticultural insecticide of the present invention may be used in admixture with other agricultural and horticultural insecticides, acaricides, nematicides, fungicides, biotic pesticides or the like in order to expand both spectrum of controllable insect pest species and the period of time when effective application are possible or to reduce the dosage. Furthermore, the agricultural and horticultural chemical of the present invention may be used in admixture with herbicides, plant growth regulators, fertilizers or the like, depending upon application situations.

As the other agricultural and horticultural insecticides, acaricides and nematicides, which are used for the above purpose, there can be exemplified agricultural and horticultural insecticides, acaricides and nematicides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylpatathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifosmethyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fostietane, Dichiofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Flucythrinate, Fluvalinate, Cycloprothrin, Ethofenprox, Halfenprox, Silafluofen, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosuifan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfiuazuron, Fenbutatin oxide, tricyclohexyltin hydroxide, sodium oleate, potassium oleate, Methoprene, Hydroprene, Binapacryl, Amitraz, Dicofol, Chrorobenzilate, Bromopropylate, Tetradifon, Bensultap, Benzoximate, Tebufenozide, Methoxyfenozide, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, nicotine sulfate, Nitenpyram, Acetamiprid, Thiacloprid, Imidacloprid, Thiamethoxam, Clothianidin, Nidinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, hydroxypropyl starch, Levamisole hydrochloride, Metamsodium, Morantel tartrate, Dazomet, Trichlamide, *Pasteuria penetrans*, Monacrosporium-phymatophagum, etc. As the agricultural and horticultural fungicides used for the same purpose as above, there can be exemplified agricultural and horticultural fungicides such as sulfur, lime sulfur, copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil (NNF-9425), Himexazol, Etridiazol, Fluoroimide, Procymidone, Vinclozolin, Iprodione, Triadimefon, Triflumizole, Bitertanol, Ipconazole, Fluconazole, Propiconazole, Dipbenoconazole, Myclobutanil, Tetraconazole, Hexaconazole, Tebuconazole, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl (CGA-245704), Fthalide, Tricyclazole, Pyroquilon, Chinomethionat, Oxolinic acid, Dithianon, Kasugamycin, Validamycin, Polyoxin, Blasticidin, Streptomycin, etc. Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacet-methyl, Quizalofop-ethyl, Bentazon, calcium peroxide, etc.

As to the biotic pesticides, the same effect as above can be expected by using the agricultural and horticultural chemical of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobactor*, non-pathogenic *Erwinia carotovora, Bacillus subtilis*, etc.; and biotic pesticides utilized as herbicides, such as *Xanthomonas campestris*, etc.

In addition, the agricultural and horticultural chemical of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl=acetate. (E,Z)-4,10-tetradecadienyl=acetate. (Z)-8-dodecenyl=acetate. (Z)-11-tetradecenyl=acetate. (Z)-13-icosen-10-one, (Z)-8-dodecenyl=acetate. (Z)-11-tetradecenyl=acetate. (Z)-13-icosen-10-one. 14-methyl-1-octadecene, etc.

Typical examples of the present invention are described below but they should not be construed as limiting the scope of the invention.

EXAMPLES

Production Example 1

(1-1). Production of 3-iodo-N- (4-heptafluoroisopropyl-2-methylphenyl)phthalamic acid A solution of 3.5 g of 4-heptafluoro-isopropyl-2-methylaniline in 3 ml of acetonitrile was slowly dropped into a suspension of 3.5 g of 1-iodophthalic anhydride in 30 ml of acetonitrile under ice-cooling. After completion of the dropwise addition, the reaction was carried out with stirring at room temperature for 3 hours. After completion of the reaction, the crystals precipitated were collected by filtration and washed with a small volume of acetonitrile to obtain 4.0 g of the desired compound.

Physical property: m.p. 174-181° C. Yield: 57%.

(1-2). Production of 3-iodo-N-(4-heptafluoroisopropyl-2-methylphenyl)phthalisoimide To a suspension of 2.0 g of 3-iodo-N-(4-heptafluoroisopropyl-2-methylphenyl)phthalamic acid in 10 ml of toluene was added 1.1 g of trifluoroacetic anhydride, and the reaction was carried out with stirring at room temperature for 30 minutes. After completion of the reaction, the solvent was distilled off under reduced pressure to obtain 2.0 g of a crude product as the desired product. The desired product obtained was used in the subsequent reaction without purification.

$^1$H-NMR [CDCl$_3$/TMS, δ values (ppm)] 2.4(s, 3H), 7.3(d, 1H), 7.4(m, 2H), 7.5 (t, 1H), 8.1(d, 1H), 8.2(d, 1H)

(1-3). Production of 3-iodo-N'-(4-heptafluoroisopropyl-2-methylphenyl)-N$^2$-[1-methyl-2-(N,N-dimethyl sulfamoylamino)ethyl]phthalamide (compound No. 45)

In 30 ml of acetonitrile was dissolved 0.4 g of 3-iodo-N-(4-heptafluoroisopropyl-2-methylphenyl)-phthalisoimide, followed by adding thereto 0.2 g of N,N-dimethylamino-N'-(2-aminopropyl)sulfonamide, and the resulting mixture was stirred at room temperature for 5 hours. After completion of the reaction, the reaction mixture was poured into ice water, followed by extraction with ethyl acetate. The organic layer was washed with an aqueous sodium chloride solution, dried over anhydrous magnesium sulfate and then distilled under reduced pressure to remove the solvent, and the resulting residue was purified by silica gel column chromatography to obtain 0.2 g of the desired compound.

Physical property: m.p. 95° C. Yield: 40%.

Production Example 2

Production of 3-iodo-N$^1$-(4-heptafluoro-isopropyl-2-methylphenyl)-N$^2$-[1-methyl-2-(ethylamino-carbonyloxy)ethyl]phthalamide (compound No. 96)

In 30 ml of acetonitrile was dissolved 0.55 g of 6-iodo-N-[1-methyl-2-(ethylaminocarbonyloxy)ethyl]-phthalisoimide, followed by adding thereto 0.38 g of 4-heptafluoroisopropyl-2-methylaniline, and the resulting mixture was stirred at room temperature for 3 hours. After completion of the reaction, the reaction mixture was poured into ice water, followed by extraction with ethyl acetate. The organic layer was washed with an aqueous sodium chloride solution, dried over anhydrous magnesium sulfate and then distilled under reduced pressure to remove the solvent, and the resulting residue was purified by silica gel column chromatography to obtain 0.36 g of the desired compound.

Physical property: m.p. 185° C. Yield: 38%.

Production Example 3

(3-1). Production of 3-iodo-N-(4-heptafluoroisopropyl-2-methylphenyl)phthalimide To a suspension of 2.7 g of 3-iodophthalic anhydride in 30 ml of acetic acid was added 2.7 g of 4-heptafluoroisopropyl-2-methylaniline, and the resulting mixture was heated under reflux for 3 hours.

After completion of the reaction, the solvent was distilled off under reduced pressure from the reaction mixture, and the resulting residue was purified by silica gel column chromatography to obtain 4.8 g of the desired compound.

Yield: 89%.

(3-2). Production of 3-iodo-N$^1$-(4-heptafluoroisopropyl-2-methylphenyl)-N$^2$-[3-t-butoxycarbonyl aminopropyl)phthalamide (compound No. 20)

In 20 ml of dioxane was dissolved 0.5 g of 3-iodo-N-(4-heptafluoroisopropyl-2-methylphenyl)-phthalimide, followed by adding thereto 0.25 g of t-butyl N-(3-aminopropyl) carbamate and two drops of trifluoroacetic acid, and the resulting mixture was stirred at room temperature for 10 hours. After completion of the reaction, the reaction mixture was poured into ice water, followed by extraction with ethyl acetate. The organic layer was washed with an aqueous sodium chloride solution, dried over anhydrous magnesium sulfate and then distilled under reduced pressure to remove the solvent, and the resulting residue was purified by silica gel column chromatography to obtain 0.2 g of the desired compound.

Physical property: m.p. 145° C. Yield: 30%.

Typical formulation examples and test examples of the present invention are described below but they should not be construed as limiting the scope of the invention.

In the formulation examples, parts are all by weight.

Formulation Example 1

| | |
|---|---|
| Each compound listed in Table 1 or Table 2 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Table 1 or Table 2 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Table 1 or Table 2 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Table 1 or Table 2 | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal effect on diamondback moth (*Plutella xylostella*)

Adult diamondback moths were released and allowed to oviposit on a Chinese cabbage seedling. Two days after the release, the seedling having eggs deposited thereon was immersed for about 30 seconds in a liquid chemical prepared by diluting a preparation containing each compound listed in Table 1 or Table 2, as an active ingredient to adjust the concentration to 50 ppm. After air-drying, the seedling was allowed to stand in a room thermostated at 25° C.

Six days after the immersion in the liquid chemical, the hatched insects were counted and the mortality was calculated according to the following equation, whereby the insecticidal effect was judged according to the criterion shown below. The test was carried out with three replications of 10 insects.

$$\text{Corrected mortality}(\%) = \frac{\begin{bmatrix}\text{Number of}\\\text{hatched insects}\\\text{in untreated}\\\text{group}\end{bmatrix} - \begin{bmatrix}\text{Number of}\\\text{hatched insects}\\\text{in treated}\\\text{group}\end{bmatrix}}{\begin{bmatrix}\text{Number of}\\\text{hatched insects in}\\\text{untreated group}\end{bmatrix}} \times 100$$

Criterion for Judgment
 A—mortality 100%
 B—mortality 99% to 90%
 C—mortality 89% to 80%
 D—mortality 79% to 50%

As a result of the above test, it was found that the following compounds had an insecticidal activity rated B or higher: compound Nos. 1 to 122, 127 to 130, 133 to 136, 139, 140, 142 to 145, 148, 149, 152, 153, 157, 161, 165, 167 to 173, 182 to 185, 194, 198, 199, 204, 205, 210 to 212, 214 to 216, 222, 223, 229, 230, 235, 236, 243, 247, 259, 260, 263 to 272, 274, 275, 278 to 280, 284 to 290, 293, 297, 308, 311, 312, 317 to 322, 2-3,2-5, 2-11, 2-13, 2-28, 2-29, 2-32, 2-33, 2-35, 2-39, 2-47 to 2-52, 2-72, 2-73 and 2-74.

Test Example 2

Insecticidal effect on common cutworm (*Spodoptera litura*)

A piece of cabbage leaf (cultivar: Shikidori) was immersed for about 30 seconds in a liquid chemical prepared by diluting a preparation containing each compound listed in Table 1 or Table 2, as an active ingredient to adjust the concentration to 50 ppm. After air-drying, the piece was placed in a plastic Petri dish with a diameter of 9 cm and inoculated with second-instar larvae of common cutworm, after which the dish was closed and then allowed to stand in a room thermostated at 25° C. Eight days after the inoculation, the dead and alive were counted and the mortality was calculated according to the following equation, whereby the insecticidal effect was judged according to the criterion shown in Test Example 1. The test was carried out with three replications of 10 insects.

$$\text{Corrected mortality}(\%) = \frac{\begin{bmatrix}\text{Number of}\\\text{alive insects}\\\text{in untreated}\\\text{group}\end{bmatrix} - \begin{bmatrix}\text{Number of}\\\text{alive insects}\\\text{in treated}\\\text{group}\end{bmatrix}}{\begin{bmatrix}\text{Number of}\\\text{alive insects in}\\\text{untreated group}\end{bmatrix}} \times 100$$

As a result of the above test, it was found that the following compounds had an activity rated B or higher: compound Nos. 1, 2, 6 to 9, 12 to 16, 19, 22, 28, 29, 33 to 36, 38 to 45, 48, 50, 51, 54 to 57, 59, 62 to 72, 74, 76 to 78, 81 to 86, 88, 90 to 113, 116, 117, 129, 130, 133, 134, 139, 142, 144, 148, 152, 153, 172, 184, 229, 247, 272, 274, 279, 286, 287, 289, 290, 2-32, 2-35, 2-39, 2-47, 2-49 to 2-51, 2-72 and 2-73.

Test Example 3

Insecticidal effect on smaller tea tortrix (*Adoxophyes* sp.)

Tea leaves were immersed for about 30 seconds in a liquid chemical prepared by diluting a preparation containing each compound listed in Table 1 or Table 2, as an active ingredient to adjust the concentration to 50 ppm. After air-drying, the tea leaves were placed in a plastic Petri dish with a diameter of 9 cm and inoculated with larvae of smaller tea tortrix, after which the dish was allowed to stand in a room thermostated at 25° C. and having a humidity of 70%. Eight days after the inoculation, the dead and alive were counted and the insecticidal effect was judged according to the criterion shown in Test Example 1. The test was carried out with three replications of 10 insects.

As a result of the above test, it was found that the following compounds had an activity rated B or higher: compound Nos. 1 to 4, 6 to 10, 12 to 16, 19 to 26, 28 to 45, 48 to 51, 54 to 60, 62 to 72, 74 to 78, 80 to 117, 129, 130, 133 to 136, 139, 140, 142, 144, 145, 148, 149, 152, 153, 170, 182, 184, 210, 247, 265, 272, 274, 279, 284, 286, 287, 289, 290, 317, 322, 2-32, 2-35, 2-39, 2-47, 2-49 to 2-51, 2-72 and 2-73.

What is claimed is:
1. An aromatic diamide derivative represented by the general formula (I):

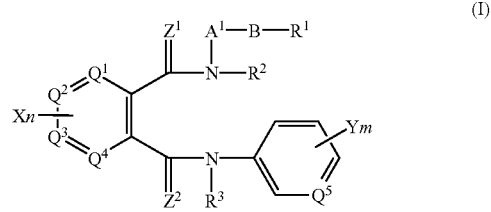

{wherein $A^1$ is a $(C_1-C_8)$alkylene group; a substituted $(C_1-C_8)$alkylene group having one or more substituents which may be the same or different and are selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, $(C_1-C_6)$alkyl-thio$(C_1-C_6)$alkyl groups, $(C_1-C_6)$alkoxycarbonyl groups and phenyl group; a $(C_3-C_8)$alkenylene group; a substituted $(C_3-C_8)$alkenylene group having one or more substituents which may be the same or different and are selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkylsulfonyl groups, halo$(C_1-C_6)$alkylsulfonyl groups, $(C_1-C_6)$alkylthio$(C_1-C_6)$alkyl groups, $(C_1-C_6)$alkoxycarbonyl groups and phenyl group; a $(C_3-C_8)$alkynylene group; or a substituted $(C_3-C_8)$alkynylene group having one or more substituents which may be the same or different and are selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkylsulfonyl groups, halo$(C_1-C_6)$alkyl-sulfonyl groups, $(C_1-C_6)$alkylthio$(C_1-C_6)$alkyl groups, $(C_1-C_6)$alkoxycarbonyl groups and phenyl group, any of the saturated carbon atoms in the above-mentioned $(C_1-C_8)$alkylene group, substituted $(C_1-C_8)$alkylene group, $(C_3-C_8)$alkenylene group, substituted $(C_3-C_8)$alkenylene group, $(C_3-C_8)$alkynylene group or substituted $(C_3-C_8)$alkynylene group being able to have a $(C_2-C_5)$alkylene group bonded thereto as a substituent, to form a $(C_3-C_6)$cycloalkane ring, and any two of the carbon atoms in the above-mentioned $(C_1-C_8)$alkylene group, substituted $(C_1-C_8)$alkylene group, $(C_3-C_8)$alkeny-lene group and substituted $(C_3-C_8)$alkenylene group being able to form a $(C_3-C_6)$cycloalkane ring or a $(C_3-C_6)$cyclo-alkene ring together with an alkylene group or an alkenylene group, B is —O—

$R^1$ is —C(=WQ$^1$)—N(R$^5$)(R$^6$) (wherein W$^1$ is an oxygen atom or a sulfur atom, and each of R$^5$ and R$^6$, which may be the same or different, is a hydrogen atom; a $(C_1-C_6)$alkyl group; a halo$(C_1-C_6)$alkyl group; a $(C_1-C_4)$alkoxy$(C_1-C_4)$alkyl group; a $(C_1-04)$alkylthio$(C_1-C_4)$alkyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_1-C_6)$alkyl-sulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenyl$(C_1-C_4)$alkyl group; a substituted phenyl$(C_1-C_4)$alkyl group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkylsulfonyl groups, halo$(C_1-C_6)$alkyl-sulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, further, $R^5$ being able to bind to $R^6$ to form a 5- to 8-membered ring that may contain one or two atoms which may be the same or different and are selected from oxygen atom, sulfur atom and nitrogen atom, between adjacent carbon atoms constituting the ring);

each of $R^2$ and $R^3$, which may be the same or different, is a hydrogen atom, a $(C_3-C_6)$cycloalkyl group or —A$^2$—R$^8$ (wherein A$^2$ is —C(=O)—, —C(=S)—, —C(=NR$^9$)— (wherein R$^9$ is a hydrogen atom, a $(C_1-C_6)$alkyl group, a $(C_1-C_6)$alkoxy group, a mono$(C_1-C_6)$alkylamino group, a di$(C_1-C^6)$alkylamino group whose $(C_1-C_6)$alkyl groups may be the same or different, a $(C_1-C_6)$alkoxycarbonyl group, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkylsulfonyl groups, halo$(C_1-C_6)$alkyl-sulfonyl groups, mono$(C_1-C_6)$alkylamino groups, di$(C^1-C_6)$alkylamino groups whose $(C_1-C_6)$alkyl groups may be the same or different, and $(C_1-C_6)$alkoxycarbonyl groups), a $(C_1$-08$)$alkylene group, a halo$(C_1-C_8)$alkylene group, a $(C_3-C_6)$alkenylene group, a halo$(C_3-C_6)$alkenylene group, a $(C_3-C_6)$alkynylene group or a halo$(C_3-C_6)$alkynylene group, (1) in the case of $A^2$ being C—(=O)—, —C(=S)— or —C(=NR$^9$)—(wherein R$^9$ is as defined above), R$^8$ is a hydrogen atom; a —$(C_1-C_6)$alkyl group; a halo$(C_1-C_6)$alkyl group; a $(C_3-C_6)$cycloalkyl group; a halo$(C_3-C_6)$cycloalkyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1C_6)$alkoxy groups, $(C_1-C_6)$alkylthio groups, halo$(C_1-C_6)$alkylthio groups, $(C_1-C_6)$alkyl-sulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; or —$A^3$—$R^{10}$ (wherein $A^3$ is —O—, —S— or —N($R^{11}$) (wherein $R^{11}$ is a hydrogen atom; a $(C_1-C_6)$alkylcarbonyl group; a halo$(C_1-C_6)$alkylcarbonyl group; a $(C_1-C_6)$alkoxycarbonyl group; a phenylcarbonyl group; a substituted phenylcarbonyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C^1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenyl$(C_1-C_4)$alkoxycarbonyl group; or a substituted phenyl$(C_1-C_4)$alkoxycarbonyl group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkyl-sulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups), and $R^{10}$ is a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_3-C_6)$cycloalkyl group; a halo$(C_3-C_6)$cycloalkyl group; a $(C_1-C_6)$alkylcarbonyl group; a halo$(C_1-C_6)$alkylcarbonyl group; a $(C_1-C_6)$alkoxycarbonyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_1-C_6)$alkyl-sulfinyl groups, halo$(C_1-C_6)$alkylsulfinyl groups, $(C_1-C_6)$alkylsulfonyl groups, halo$(C_1-C_6)$alkylsulfonyl groups, mono$(c_1-C_6)$alkylamino groups, di$(C_1-C_6)$alkylamino groups whose $(C_1-C_6)$alkyl groups may be the same or different, and $(C_1-C_6)$alkoxycarbonyl groups; a phenyl$(C_1-C_4)$alkyl group; a substituted phenyl$(C_1-C_4)$alkyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_1-C_6)$alkyl-sulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkyl-sulfinyl groups, halo$(C_1$-06$)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups), (2) in the case of $A^2$ being a $(C_1-C_8)$alkylene group, a halo$(C_1-C_8)$alkylene group, a $(C_3-C_6)$alkenylene group, a halo$(C_3-C_6)$alkenylene group, a $(C_3-C_6)$alkynylene group or a halo$(C_3-C_6)$alkynylene group, $R^8$ is a hydrogen atom; a halogen atom; a cyano group; a nitro group; a $(C_3-C_6)$cycloalkyl group; a halo$(C_3-C_6)$cycloalkyl group; a $(C_1-C_6)$alkoxycarbonyl group; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkyl-sulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_1-C_6)$alkyl-sulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; or —$A^4$—$R^{12}$ (wherein $A^4$ is —O—, —S—, —SO—, —$SO_2$—, —N($R^{11}$)— (wherein $R^{11}$ is as defined above), —C(=O)—, or —C(=N—O$R^{13}$) (wherein $R^{13}$ is a hydrogen atom, a $(C_1-C_6)$alkyl group, a halo$(C_1-C_6)$alkyl group, a $(C_3-C_6)$alkenyl group, a halo$(C_3-C_6)$alkenyl group, a $(C_3-C_6)$alkynyl group, a halo$(C_3-C_6)$alkynyl group, a $(C_3-C_6)$cycloalkyl group, a phenyl$(C_1-C_4)$alkyl group, or a substituted phenyl$(C_1-C_4)$alkyl group having on the ring one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkyl-sulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups), (i) in the case of $A^4$ being —O—, —S—, —SO—, —$SO_2$— or —N($R^{11}$)— (wherein $R^{11}$ is as defined above), $R^{12}$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a ($C_3$-$C_6$)cycloalkyl group; a halo($C_3$-$C_6$)cycloalkyl group; a ($C_1$-$C_6$)alkylcarbonyl group; a halo($C_1$-$C_6$)alkyl-carbonyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, (ii) in the case of $A^4$ being —C(=O)— or —C(=NOR$^{13}$) (wherein $R^{13}$ is as defined above), $R^{12}$ is a hydrogen atom; a ($C_1$-$C_6$)alkyl group; a halo($C_1$-$C_6$)alkyl group; a ($C_2$-$C_6$)alkenyl group; a halo($C_2$-$C_6$)alkenyl group; a ($C_3$-$C_6$)cycloalkyl group; a halo($C_3$-$C_6$)cycloalkyl group; a ($C_1$-$C_6$)alkoxy group; a halo($C_1$-$C_6$)alkoxy group; a ($C_1$-$C_6$)alkylthio group; a halo($C_1$-$C_6$)alkylthio group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylamino group; a substituted phenylamino group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyloxy group; a substituted phenyloxy group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups; a phenylthio group; a substituted phenylthio group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups)), further, $R^2$ being able to bind to $A^1$ or $R^1$ to form a 5- to 8-membered ring that may contain one to three atoms which may be the same or different and are selected from oxygen atom, sulfur atom and nitrogen atom, between adjacent carbon atoms constituting the ring, each of $Q^1$ through $Q^5$ is a carbon atom or a nitrogen atom, each of Xs, which may be the same or different, is a halogen atom; a cyano group; a nitro group; a ($C_3$-$C_6$) cycloalkyl group; a halo($C_3$-$C_6$)cycloalkyl group; a ($C_1$-$C_6$)alkoxycarbonyl group; a phenyl group; a substituted phenyl group having one or more substituents which may be the same or different and are selected from halogen atoms, cyano group, nitro group, ($C_1$-$C_6$) alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo ($C_1$-$C_6$)alkoxy groups, ($C_1$-$C_6$)alkyl-thio groups, halo ($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^5$—$R^{14}$ (wherein $A^5$ is —O—, —S—, —SO—, —$SO_2$—, —C(=O)—, —C(=NOR$^{13}$) (wherein R$^{13}$ is as defined above), a (C$_1$-C$_6$)alkylene group, a halo(C$_1$-C$_6$)alkylene group, a (C$_2$-C$_6$)alkenylene group, a halo(C$_2$-C$_6$)alkenylene group, a (C$_2$-C$_6$)alkynylene group or a halo(C$_3$-C$_6$)alkynylene group, (1) in the case of A$^5$ being —O—, —S—, —SO— or —SO$_2$—, R$^{14}$ is a halo(C$_3$-C$_6$)cycloalkyl group; a halo(C$_3$-C$_6$)cycloalkenyl group; a phenyl group; a substituted phenyl group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkylthio groups, halo(C$_1$-C$_6$)alkylthio groups, (C$_1$-C$_6$)alkylsulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; a heterocyclic group; a substituted heterocyclic group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkyl-thio groups, halo(C$_1$-C$_6$)alkylthio groups, (C$_1$-C$_6$)alkyl-sulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; or —A$^6$—R$^{15}$ (wherein A$^6$ is a (C$_1$-C$_6$)alkylene group, a halo(C$_1$-C$_6$)alkylene group, a (C$_3$-C$_6$)alkenylene group, a halo(C$_3$-C$_6$)alkenylene group, a (C$_3$-C$_6$)alkynylene group or a halo(C$_3$-C$_6$)alkynylene group, and R$^{15}$ is a hydrogen atom; a halogen atom; a (C$_3$-C$_6$)cycloalkyl group; a halo(C$_3$-C$_6$)cycloalkyl group; a (C$_1$-C$_6$)alkoxycarbonyl group; a phenyl group; a substituted phenyl group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkylthio groups, halo(C$_1$-C$_6$)alkylthio groups, (C$_1$-C$_6$)alkylsulfinyl groups, halo(C$_1$-C$_6$)alkylsulfinyl groups, (C$_1$-C$_6$)alkyl-sulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; or —A$^7$—R$^{16}$ (wherein A$^7$ is —O—, —S—, —SO— or —SO$_2$—, and R$^{16}$ is a (C$_1$-C$_6$)alkyl group; a halo(C$_1$-C$_6$)alkyl group; a (C$_3$-C$_6$)alkenyl group; a halo(C$_3$-C$_6$)alkenyl group; a (C$_3$-C$_6$)alkynyl group; a halo(C$_3$-C$_6$)alkynyl group; a (C$_3$-C$_6$)cycloalkyl group; a halo(C$_3$-C$_6$)cycloalkyl group; a phenyl group; a substituted phenyl group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkylthio groups, halo(C$_1$-C$_6$)alkylthio groups, (C$_1$-C$_6$)alkylsulfinyl groups, halo(C$_1$-C$_6$)alkylsulfinyl groups, (C$_1$-C$_6$)alkyl-sulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; a heterocyclic group; or a substituted heterocyclic group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkyl-thio groups, halo(C$_1$-C$_6$)alkylthio groups, (C$_1$-C$_6$)alkyl-sulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups), (2) in the case of A$^5$ being —C(=O)— or —C(=NOR$^{13}$)— (wherein R$^{13}$ is as defined above), R$^{14}$ is a (C$_1$-C$_6$)alkyl group; a halo(C$_1$-C$_6$)alkyl group; a (C$_2$-C$_6$)alkenyl group; a halo(C$_2$-C$_6$)alkenyl group; a (C$_3$-C$_6$)cycloalkyl group; a halo(C$_3$-C$_6$)cycloalkyl group; a (C$_1$-C$_6$)alkoxy group; a (C$_1$-C$_6$)alkylthio group; a mono(C$_1$-C$_6$)alkylamino group; a di(C$_1$-C$_6$)alkylamino group whose (C$_1$-C$_6$)alkyl groups may be the same or different; a phenyl group; a substituted phenyl group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkyl-thio groups, halo(C$_1$-C$_6$)alkylthio groups, (C$_1$-C$_6$)alkyl-sulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; a phenylamino group; a substituted phenylamino group having on the ring one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkylthio groups, halo(C$_1$-C$_6$)alkylthio groups, (C$_1$-C$_6$)alkylsulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups; a heterocyclic group; or a substituted heterocyclic group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo(C$_1$-C$_6$)alkoxy groups, (C$_1$-C$_6$)alkyl-thio groups, halo(C$_1$-C$_6$)alkylthio groups, (C$_1$-C$_6$)alkyl-sulfinyl groups, halo(C$_1$-C$_6$)alkylsulfinyl groups, (C$_1$-C$_6$)alkylsulfonyl groups, halo(C$_1$-C$_6$)alkylsulfonyl groups, mono(C$_1$-C$_6$)alkylamino groups, di(C$_1$-C$_6$)alkylamino groups whose (C$_1$-C$_6$)alkyl groups may be the same or different, and (C$_1$-C$_6$)alkoxycarbonyl groups, (3) in the case of A$^5$ being a (C$_1$-C$_6$)alkylene group, a halo(C$_1$-C$_6$)alkylene group, a (C$_2$-C$_6$)alkenylene group, a halo(C$_2$-C$_6$)alkenylene group, a (C$_2$-C$_6$)alkynylene group or a halo(C$_3$-C$_6$)alkynylene group, R$^{14}$ is a hydrogen atom; a halogen atom; a (C$_3$-C$_6$)cycloalkyl group; a halo(C$_3$-C$_6$)cycloalkyl group; a (C$_1$-C$_6$)alkoxycarbonyl group; a phenyl group; a substituted phenyl group having one or more substituents which may be the same or different and are selected from halogen atoms, cyano group, nitro group, (C$_1$-C$_6$)alkyl groups, halo(C$_1$-C$_6$)alkyl groups, (C$_1$-C$_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo ($C_1$-$C_6$)alkoxy groups, ($C_1$-$C_6$)alkylthio groups, halo ($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^8$—$R^7$ (wherein $A^8$ is —O—, —S—, —SO— or —$SO_2$, and $R^{17}$ is a ($C_3$-$C_6$)cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo ($C_1$-$C_6$)alkoxy groups, ($C_1$-$C_6$)alkyl-thio groups, halo ($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$) alkylsulfinyl groups, ($C_1$-$C_6$)alkylsulfonyl groups, halo ($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups; or —$A^9$—$R^{18}$ (wherein $A^9$ is a ($C_1$-$C_6$)alkylene group, a halo($C_1$-$C_6$)alkylene group, a ($C_2$-$C_6$)alkenylene group, a halo($C_2$-$C_6$)alkenylene group, a ($C_2$-$C_6$)alkynylene group or a halo($C_3$-$C_6$) alkynylene group, and $R^{18}$ is a hydrogen atom; a halogen atom; a ($C_3$-$C_6$)cycloalkyl group; a halo($C_3$-$C_6$)cycloalkyl group; a ($C_1$-$C_6$)alkoxy group; a halo ($C_1$-$C_6$)alkoxy group; a ($C_1$-$C_6$)alkylthio group; a halo ($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups, halo($C_1$-$C_6$)alkoxy groups, ($C_1$-$C_6$) alkylthio groups, halo($C_1$-$C_6$)alkylthio groups, ($C_1$-$C_6$) alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups; a phenyloxy group; a substituted phenyloxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo ($C_1$-$C_6$)alkoxy groups, ($C_1$-$C_6$)alkylthio groups, halo ($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylthio group; a substituted phenylthio group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups; a heterocyclic group; or a heterocyclic group having one or more substituents which may be the same or different and are selected from halogen atoms, cyano group, nitro group, ($C_1$-$C_6$) alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$) alkylamino groups whose ($C_1$-$C_6$)alkyl groups may be the same or different, and ($C_1$-$C_6$)alkoxycarbonyl groups)), n is an integer of 0 to 4, further, two adjacent Xs on the aromatic ring being able to be taken together to represent a fused ring that may have one or more substituents, which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$) alkoxy groups, ($C_1$-$C_6$)alkylthio groups, halo($C_1$-$C_6$) alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, each of Ys, which may be the same or different, is a halogen atom; a cyano group; a nitro group; a ($C_3$-$C_6$) cycloalkyl group; a halo($C_3$-$C_6$)cycloalkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups; a heterocyclic group; a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)

alkoxy groups, halo($C_1$-$C_6$)alkoxy groups, ($C_1$-$C_6$) alkylthio groups, halo($C_1$-$C_6$)alkylthio groups, ($C_1$-$C_6$) alkylsulfinyl groups, halo($C_1$-$C_6$)alkylsulfinyl groups, ($C_1$-$C_6$)alkylsulfonyl groups, halo($C_1$-$C_6$)alkyl-sulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; or —$A^5$—$R^{14}$ (wherein $A^5$ and $R^{14}$ are as defined above), further, two adjacent Ys on the aromatic ring being able to be taken together to represent a fused ring that may have one or more substituents which may be the same or different and are selected from halogen atoms; ($C_1$-$C_6$)alkyl groups; halo($C_1$-$C_6$)alkyl groups; ($C_1$-$C_6$) alkoxy groups; halo($C_1$-$C_6$)alkoxy groups; ($C_1$-$C_6$) alkyl-thio groups; halo($C_1$-$C_6$)alkylthio groups; ($C_1$-$C_6$)alkyl-sulfinyl groups; halo($C_1$-$C_6$)alkylsulfinyl groups; ($C_1$-$C_6$)alkylsulfonyl groups; halo($C_1$-$C_6$) alkylsulfonyl groups; phenyl group; substituted phenyl groups having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo ($C_1$-$C_6$)alkoxy groups, ($C_1$-$C_6$)alkyl-thio groups, halo ($C_1$-$C_6$)alkylthio groups, ($C_1$-$C_6$)alkyl-sulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; heterocyclic groups; and substituted heterocyclic groups having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkyl-thio groups, halo($C_1$-$C_6$)alkylthio groups, ($C_1$-$C_6$)alkyl-sulfinyl groups, halo($C_1$-$C_6$) alkylsulfinyl groups, ($C_1$-$C_6$)alkylsulfonyl groups, halo ($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups, m is an integer of 1 to 5, and each of $Z^1$ and $Z^2$ is an oxygen atom or a sulfur atom} or a salt thereof, 2. An aromatic diamide derivative or a salt thereof according to claim 1, wherein $A^1$ is a ($C_2$-$C_8$)alkylene group; a substituted ($C_2$-$C_8$)alkylene group having one or more substituents which may be the same or different and are selected from halogen atoms, cyano group, nitro group, halo($C_1$-$C_6$) alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, ($C_1$-$C_6$)alkylthio($C_1$-$C_6$)alkyl groups, ($C_1$-$C_6$)alkoxycarbonyl groups and phenyl group; a ($C_3$-$C_8$) alkenylene group; a substituted ($C_3$-$C_8$)alkenylene group having one or more substituents which may be the same or different and are selected from halogen atoms, cyano group, nitro group, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, ($C_1$-$C_6$)alkylthio ($C_1$-$C_6$)alkyl groups, ($C_1$-$C_6$)alkoxycarbonyl groups and phenyl group; a ($C_3$-$C_8$)alkynylene group; or a substituted ($C_3$-$C_8$)alkynylene group having one or more substituents which may be the same or different and are selected from halogen atoms, cyano group, nitro group, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, ($C_1$-$C_6$)alkylthio($C_1$-$C_6$)alkyl groups, ($C_1$-$C_6$) alkoxycarbonyl groups and phenyl group, any of the saturated carbon atoms in the above-mentioned ($C_2$-$C_8$)alkylene group, substituted ($C_2$-$C_8$)alkylene group, ($C_3$-$C_8$)alkenylene group, substituted ($C_3$-$C_8$) alkenylene group, ($C_3$-$C_8$)alkynylene group or substituted ($C_3$-$C_8$)alkynylene group being able to have a ($C_2$-$C_5$)alkylene group bonded thereto as a substituent, to form a ($C_3$-$C_6$)cycloalkane ring, and any two of the carbon atoms in the above-mentioned ($C_2$-$C_8$)alkylene group, substituted ($C_2$-$C_8$)alkylene group, ($C_3$-$C_8$)alkenylene group and substituted ($C_3$-$C_8$)alkenylene group being able to form a ($C_3$-$C_6$)cycloalkane ring or a ($C_3$-$C_6$)cycloalkene ring together with an alkylene group or an alkenylene group, B is —O—

$R^1$ is

—C(=$W^1$)—N($R^5$)($R^6$) (wherein $W^1$ is an oxygen atom or a sulfur atom, and each of $R^5$ and $R^6$, which may be the same or different, is a hydrogen atom; a ($C_1$-$C_6$) alkyl group; a halo($C_1$-$C_6$)alkyl group; a ($C_1$-$C_4$)alkoxy ($C_1$-$C_4$)alkyl group; a ($C_1$-$C_4$)alkylthio($C_1$-$C_4$)alkyl group; a phenyl group; a substituted phenyl group having one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$) alkoxy groups, ($C_1$-$C_6$)alkylthio groups, halo($C_1$-$C_6$) alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_4$)alkyl group; a substituted phenyl($C_1$-$C_4$)alkyl group having on the ring one or more substituents which may be the same or different and are selected from halogen atoms, cyano group, nitro group, ($C_1$-$C_6$)alkyl groups, halo ($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo ($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups), each of $R^2$ and $R^3$, which may be the same or different, is a hydrogen atom or a ($C_1$-$C_3$)alkyl group, each of $Q^1$ through $Q^5$ is a carbon atom or a nitrogen atom, each of Xs, which may be the same or different, is a halogen atom, a nitro group, a $(C_1$-$C_6)$alkyl group, a halo$(C_1$-$C_6)$alkyl group, a $(C_2$-$C_6)$alkenyl group, a halo$(C_2$-$C_6)$alkenyl group, a $(C_2$-$C_6)$alkynyl group, a halo$(C_2$-$C_6)$alkynyl group, a $(C_1$-$C_6)$alkoxy group, a halo$(C_1$-$C_6)$alkoxy group, a $(C_1$-$C_6)$alkylthio group, a halo$(C_1$-$C_6)$alkylthio group, a $(C_1$-$C_6)$alkylsulfinyl group, a halo$(C_1$-$C_6)$alkylsulfinyl group, a $(C_1$-$C_6)$alkylsulfonyl group or a halo$(C_1$-$C_6)$alkylsulfonyl group, n is an integer of 0 to 2, each of Ys, which may be the same or different, is a halogen atom; a cyano group; a nitro group; a $(C_3$-$C_6)$cycloalkyl group; a halo$(C_3$-$C_6)$cycloalkyl group; a phenyl group; a substituted phenyl group having one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, di$(C_1$-$C_6)$alkylamino groups whose $(C_1$-$C_6)$alkyl groups may be the same or different, and $(C_1$-$C_6)$alkoxycarbonyl groups; or —$A^5$—$R^{14}$ (wherein $A^5$ and $R^{14}$ are as defined above), two adjacent Ys on the aromatic ring being able to be taken together to represent a fused ring that may have one or more substituents which may be the same or different and are selected from halogen atoms; $(C_1$-$C_6)$alkyl groups; halo$(C_1$-$C_6)$alkyl groups; $(C_1$-$C_6)$alkoxy groups; halo$(C_1$-$C_6)$alkoxy groups; $(C_1$-$C_6)$alkylthio groups; halo$(C_1$-$C_6)$alkylthio groups; $(C_1$-$C_6)$alkylsulfinyl groups; halo$(C_1$-$C_6)$alkylsulfinyl groups; $(C_1$-$C_6)$alkylsulfonyl groups; halo$(C_1$-$C_6)$alkylsulfonyl groups; phenyl group; substituted phenyl groups having one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, di$(C_1$-$C_6)$alkylamino groups whose $(C_1$-$C_6)$alkyl groups may be the same or different, and $(C_1$-$C_6)$alkoxycarbonyl groups; heterocyclic groups; and substituted heterocyclic groups having one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, di$(C_1$-$C_6)$alkylamino groups whose $(C_1$-$C_6)$alkyl groups may be the same or different, and $(C_1$-$C_6)$alkoxycarbonyl groups, m is an integer of 1 to 5, and each of $Z^1$ and $Z^2$ is an oxygen atom or a sulfur atom.

3. An aromatic diamide derivative or a salt thereof according to claim 2, wherein $A^1$ is a $(C_2$-$C_8)$alkylene group; a substituted $(C_2$-$C_8)$alkylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group; a $(C_3$-$C_8)$alkenylene group; a substituted $(C_3$-$C_8)$alkenylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group; a $(C_3$-$C_8)$alkynylene group; or a substituted $(C_3$-$C_8)$alkynylene group having one or more substituents which may be the same or different and are selected from halogen atoms, cyano group, nitro group, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, $(C_1$-$C_6)$alkylthio$(C_1$-$C_6)$alkyl groups, $(C_1$-$C_6)$alkoxycarbonyl groups and phenyl group, any of the saturated carbon atoms in the above-mentioned $(C_2$-$C_8)$alkylene group, substituted $(C_2$-$C_8)$alkylene group, $(C_3$-$C_8)$alkenylene group, substituted $(C_3$-$C_8)$alkenylene group, $(C_3$-$C_8)$alkynylene group or substituted $(C_3$-$C_8)$alkynylene group being able to have a $(C_2$-$C_5)$alkylene group bonded thereto as a substituent, to form a $(C_3$-$C_6)$cycloalkane ring, and any two of the carbon atoms in the above-mentioned $(C_1$-$C_8)$alkylene group, substituted $(C_1$-$C_8)$alkylene group, $(C_3$-$C_8)$alkenylene group and substituted $(C_3$-$C_8)$alkenylene group being able to form a $(C_3$-$C_6)$cycloalkane ring or a $(C_3$-$C_6)$cycloalkene ring together with an alkylene group or an alkenylene group, B is —O—

$R^1$ is

—C(=$W^1$)—N($R^5$)($R^6$) (wherein $W^1$ is an oxygen atom or a sulfur atom, and each of $R^5$ and $R^6$, which may be the same or different, is a hydrogen atom; a $(C_1$-$C_6)$alkyl group; a halo$(C_1$-$C_6)$alkyl group; a $(C_1$-$C_4)$alkoxy$(C_1$-$C_4)$alkyl group; a $(C_1$-$C_4)$alkylthio$(C_1$-$C_4)$alkyl group; a phenyl group; a substituted phenyl group having one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, di$(C_1$-$C_6)$alkylamino groups whose $(C_1$-$C_6)$alkyl groups may be the same or different, and $(C_1$-$C_6)$alkoxycarbonyl groups; a phenyl$(C_1$-$C_4)$alkyl group; a substituted phenyl$(C_1$-$C_4$alkyl group having on the ring one or more substituents which may be the same or different and are selected from halogen atoms, cyano group, nitro group, $(C_1$-$C_6)$alkyl groups, halo$(C_1$-$C_6)$alkyl groups, $(C_1$-$C_6)$alkoxy groups, halo$(C_1$-$C_6)$alkoxy groups, $(C_1$-$C_6)$alkylthio groups, halo$(C_1$-$C_6)$alkylthio groups, $(C_1$-$C_6)$alkylsulfinyl groups, halo$(C_1$-$C_6)$alkylsulfinyl groups, $(C_1$-$C_6)$alkylsulfonyl groups, halo$(C_1$-$C_6)$alkylsulfonyl groups, mono$(C_1$-$C_6)$alkylamino groups, di$(C_1$-$C_6)$alkylamino groups whose $(C_1$-$C_6)$alkyl groups may be the same or different, and $(C_1$-$C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$ alkoxycarbonyl groups), each of $R^2$ and $R^3$, which may be the same or different, is a hydrogen atom or a $(C_1-C_3)$alkyl group, each of $Q^1$ through $Q^4$ is a carbon atom, each of Xs, which may be the same or different, is a halogen atom, a nitro group, a $(C_1-C_6)$alkyl group, a halo$(C_1-C_6)$alkyl group, a $(C_2-C_6)$alkenyl group, a halo$(C_2-C_6)$alkenyl group, a $(C_2-C_6)$alkynyl group, a halo$(C_2-C_6)$alkynyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group or a halo$(C_1-C_6)$alkylsulfonyl group, n is an integer of 0 to 2, $Q^5$ is a carbon atom or a nitrogen atom, each of Ys, which may be the same or different, is a halogen atom; a $(C_1-C_6)$alkyl group; a halo$(C_1-C_6)$alkyl group; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; a halo$(C_1-C_6)$alkoxyhalo$(C_1-C_6)$alkoxy group; a phenyl group; a substituted phenyl group having one or more substituents which may be the same or different and are selected from halogen atoms, cyano group, halo$(C_1-C_6)$alkyl groups, halo$(C_1-C_6)$alkoxy groups, halo$(C_1-C_6)$alkylthio groups, halo$(C_1-C_6)$alkylsulfinyl groups and halo$(C_1-C_6)$alkylsulfonyl groups; a phenyloxy group; a substituted phenyloxy group having one or more substituents which may be the same or different and are selected from halogen atoms, cyano group, halo$(C_1-C_6)$alkyl groups, halo$(C_1-C_6)$alkoxy groups, halo$(C_1-C_6)$alkylthio groups, halo$(C_1-C_6)$alkylsulfinyl groups and halo$(C_1-C_6)$alkylsulfonyl groups;

two adjacent Ys on the aromatic ring being able to be taken together to represent a fused ring that may have one or more substituents which may be the same or different and are selected from halogen atoms, m is an integer of 1 to 3, and each of $Z^1$ and $Z^2$ is an oxygen atom.

4. An agricultural and horticultural chemical comprising an aromatic diamide derivative or a salt thereof according to claim 1 as an active ingredient.

5. An agricultural and horticultural chemical according to claim 4, which is an agricultural and horticultural insecticide.

6. A method for applying an agricultural and horticultural chemical, characterized by applying an agricultural and horticultural chemical according to claim 4 to a crop to be protected or the growth environment of the crop to be protected, in an effective dosage for protecting useful crops against insect pests.

7. A method for applying an agricultural and horticultural chemical according to claim 5 which is an agricultural and horticultural insecticide.

\* \* \* \* \*